United States Patent
Struillou et al.

(10) Patent No.: US 12,016,943 B2
(45) Date of Patent: Jun. 25, 2024

(54) ANTIPERSPIRANT OR DEODORANT COMPOSITION

(71) Applicant: Firmenich SA, Geneva (CH)

(72) Inventors: Arnaud Struillou, Geneva (CH); Daniel Reichlin, Geneva (CH)

(73) Assignee: FIRMENICH SA, Geneva (CH)

( * ) Notice: Subject to any disclaimer, the term of this patent is extended or adjusted under 35 U.S.C. 154(b) by 132 days.

(21) Appl. No.: 16/323,341

(22) PCT Filed: Aug. 25, 2017

(86) PCT No.: PCT/EP2017/071460
§ 371 (c)(1),
(2) Date: Feb. 5, 2019

(87) PCT Pub. No.: WO2018/037121
PCT Pub. Date: Mar. 1, 2018

(65) Prior Publication Data
US 2021/0315790 A1  Oct. 14, 2021

(30) Foreign Application Priority Data
Aug. 25, 2016 (EP) .................................. 16185738

(51) Int. Cl.
| | | |
|---|---|---|
| *A61K 8/46* | (2006.01) | |
| *A61K 8/02* | (2006.01) | |
| *A61K 8/04* | (2006.01) | |
| *A61K 8/11* | (2006.01) | |
| *A61Q 13/00* | (2006.01) | |
| *A61Q 15/00* | (2006.01) | |

(52) U.S. Cl.
CPC .............. *A61K 8/46* (2013.01); *A61K 8/0229* (2013.01); *A61K 8/046* (2013.01); *A61K 8/11* (2013.01); *A61Q 13/00* (2013.01); *A61Q 15/00* (2013.01); *A61K 2800/56* (2013.01); *A61K 2800/5922* (2013.01)

(58) Field of Classification Search
CPC ...................................................... A61K 8/46
See application file for complete search history.

(56) References Cited

U.S. PATENT DOCUMENTS

| | | | | |
|---|---|---|---|---|
| 7,723,286 B2* | 5/2010 | Fehr | ........................ | A61K 8/18 512/8 |
| 8,828,367 B2* | 9/2014 | Banowski | ............ | A61K 8/0229 424/65 |
| 2003/0024997 A1* | 2/2003 | Welch | ....................... | A61K 7/46 239/53 |
| 2014/0170194 A1* | 6/2014 | Cetti | ........................ | A61K 8/11 |
| 2015/0045274 A1* | 2/2015 | Fankhauser | ............... | C11D 3/50 |
| 2015/0217015 A1* | 8/2015 | Williams | .................. | A61L 9/01 |

FOREIGN PATENT DOCUMENTS

| | | | | |
|---|---|---|---|---|
| CN | 104203913 A | 12/2014 | | |
| EP | 0816322 A1 | 1/1998 | | |
| WO | WO0151599 A1 * | 7/2001 | ............... | C11D 3/50 |
| WO | 2003049666 A2 | 6/2003 | | |
| WO | 2004105713 A1 | 12/2004 | | |
| WO | 2015032885 A1 | 3/2015 | | |
| WO | 2015119813 A1 | 8/2015 | | |
| WO | 2016135193 A1 | 9/2016 | | |

OTHER PUBLICATIONS

Chemicalbook, CAS DataBase List, Aluminum Sulfate, 2017 (Year: 2017).*
International Search Report and Written Opinion for PCT Application No. PCT/EP2017/071460, dated Oct. 30, 2017.

* cited by examiner

*Primary Examiner* — Mark V Stevens
*Assistant Examiner* — Alparslan Asan
(74) *Attorney, Agent, or Firm* — Armstrong Teasdale LLP

(57) ABSTRACT

The present disclosure relates to the field of perfumery and more precisely it concerns a deodorant or an antiperspirant composition comprising a β-thio carbonyl profragrance. The use of the composition to reduce body odour and a dispensing container comprising the composition are also objects of the disclosure.

18 Claims, 9 Drawing Sheets

ANTIPERSPIRANT OR DEODORANT COMPOSITION

This application is a 371 filing of International Patent Application PCT/EP2017/071460 filed 25 Aug. 2017, which claims the benefit European patent application 16185738.8, filed 25 Aug. 2016, the contents of which are hereby incorporated by reference in their entirety.

CROSS REFERENCE TO RELATED APPLICATIONS

This application claims priority to European Patent Application Serial No. 16185738.8, filed Aug. 25, 2016, the entire contents of which is hereby incorporated by reference in its entirety.

FIELD OF THE INVENTION

The present disclosure relates to the field of perfumery. In particular, the present disclosure provides a deodorant or an antiperspirant composition comprising a perfume comprising a profragrance and free perfume. A dispensing device comprising the composition is also an object of the present disclosure.

BACKGROUND

One of the problems faced by the perfumery industry lies in the relatively rapid loss of the olfactive benefit provided by odoriferous compounds due to their volatility. The perfume industry has a particular interest for compositions or additives which are capable of prolonging or enhancing the perfuming effect of a mixture of several fragrances at the same time over a certain period of time. It is particularly desirable to obtain long-lasting properties for standard perfumery raw materials which are too volatile or have a poor substantivity by themselves, or which are only deposited in a small amount onto the surface of the final application. This problem has been addressed using delivery systems, e.g. capsules containing a perfume, to release the fragrance in a controlled manner.

One alternative to encapsulation systems is precursor compounds, also known as profragrances, which release an active material by a chemical reaction during or after application (using $O_2$, light, enzymes, water (pH) or temperature as the release trigger). An example of a profragrance is the β-thio carbonyl profragrance derivative described in WO 03/049666. The benefit of the use of the profragrance has been largely demonstrated in water-based home-care products, and more particularly in laundry products such as detergents or softeners wherein the perfume release profile has been improved.

However, deodorant compositions frequently do not provide satisfactory antiperspirant/moisture control, and/or malodour control. Therefore, there is still a need for stable deodorant compositions having acceptable malodour and antiperspirant/moisture control.

The present disclosure provides a solution to the above mentioned problems with an antiperspirant or deodorant composition comprising a liquid carrier, a perfume, and a β-thio carbonyl profragrance.

SUMMARY

One aspect presented herein provides a composition comprising:

a. a carrier;
b. a perfuming composition, comprising:
  i. at least one β-thio carbonyl derivative profragrance of formula

wherein the wavy line indicates the location of the bond between said P and the sulfur atom, P represents a group of the formulae (P-1) to (P-9), in the form of any one of their isomers:

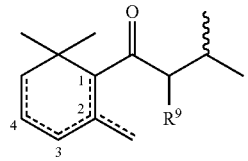
(P-1)

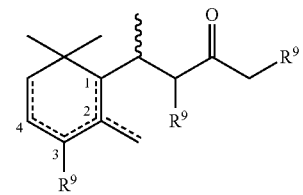
(P-2)

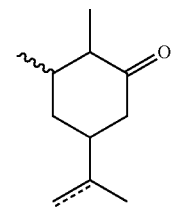
(P-3)

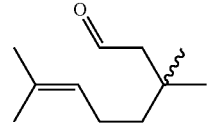
(P-4)

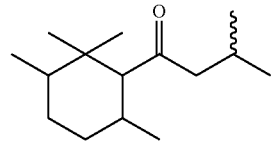
(P-5)

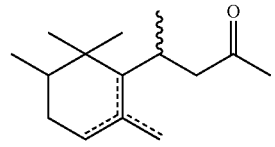
(P-6)

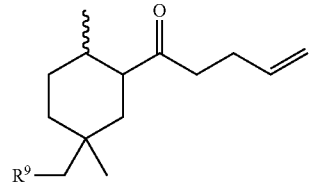
(P-7)

-continued

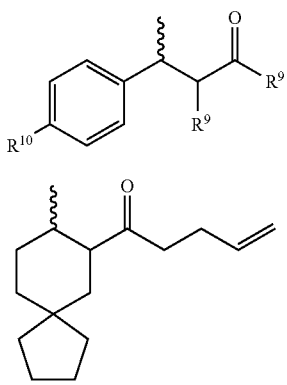

(P-8)

(P-9)

in which formulae the wavy lines have the meaning indicated above and the dotted lines represent a single or double bond, $R^9$ being a hydrogen atom or a methyl group; $R^{10}$ representing a hydrogen atom, a hydroxy or methoxy group or a C1-C4 linear or branched alkyl group, and R represents a linear or branched alkyl group having from 8 to 15 carbon atoms, optionally comprising a carboxylic functional group which is not directly linked to the sulphur atom; and ii. a free perfume,
wherein the at least one β-thio carbonyl derivative profragrance of formula (I) is present in an amount from 0.001 to 10 wt %, relative to the total weight of the composition, and
wherein the free perfume is present in an amount from 0.0001 to 6 wt %, relative to the total weight of the composition.

In one aspect, the composition further comprises an encapsulated perfume.

In one aspect, the composition further comprises an antiperspirant active.

In one aspect, the at least one β-thio carbonyl derivative profragrance of formula (I) is present in an amount from 0.001 to 7 wt %, relative to the total weight of the composition.

In one aspect, the at least one β-thio carbonyl derivative profragrance of formula (I) is present in an amount from 0.001 to 5 wt %, relative to the total weight of the composition.

In one aspect, the free perfume is present in an amount from 0.0001 to 1 wt %, relative to the total weight of the composition.

In one aspect, the β-thio carbonyl profragrance derivative of formula (I) is a derivative wherein P is a group selected from the group consisting of formulae (P-1), (P-2), (P-5) and (P-6).

In one aspect, the β-thio carbonyl profragrance derivative of formula (I) is selected from the group consisting of: 3-(dodecylthio)-1-(2,6,6-trimethylcyclohex-3-en-1-yl)butan-1-one, 3-(dodecylthio)-1-(2,6,6-trimethylcyclohex-2-en-1-yl)butan-1-one, 4-(dodecylthio)-4-(2,6,6-trimethylcyclohex-2-en-1-yl)butan-2-one, and mixtures thereof.

In one aspect, the composition is formulated as an antiperspirant or deodorant product selected from the group consisting of: a body spray formulation, a solid formulation, a roll-on formulation and an aerosol formulation.

In one aspect, the composition comprises less than 95 wt % of water, relative to the total weight of the composition.

In one aspect, the composition is water-free.

In one aspect, the liquid carrier is selected from the group consisting of: ethanol, water, a surfactant, and mixtures thereof.

In one aspect, the free perfume is selected from the group consisting of: geraniol, citronellol, dihydromyrcenol, hydroxycitronellal, 3-Methyl-5-cyclopentadecen-1-one, cyclopentadecanone, (1S,1'R)-[1-(3,3'-Dimethyl-1'-cyclohexyl)ethoxycarbonyl]methyl propanoate, pentadecenolide, 7-Methyl-2H,4H-1,5-benzodioxepin-3-one, indole, 3-methyl-4-(2,6,6-trimethyl-2-cyclohexen-1-yl)-3-buten-2-one (isoraldeine), 1-5,5-dimethylcyclohex-1-en-1-yl)pent-4-en-1-one, amyl salicylate, methyl dihydrojasmonate, cyclohexyl salicylate and mixtures thereof.

In one aspect, the free perfume comprises at least one perfuming ingredient selected from the group consisting of: 1-(octahydro-2,3,8,8-tetramethyl-2-naphtalenyl)-1-ethanone, dipropylene glycol, 2,4-Dimethyl-3-cyclohexene-1-carbaldehyde, dodecahydro-3a,6,6,9a-tetramethyl-naphtho[2,1-b]furan, linalool, coumarin, (Z)-3-hexen-1-ol, allyl amyl glycolate, 2-tert-butyl-1-cyclohexyl acetate, styrallyl acetate, 3-(4-tert-butylphenyl)-2-methylpropanal, 1,4-dioxa-5,17-cycloheptadecanedione, crystal moss, gamma undecalactone, (Z)-hex-3-en-1-yl acetate, neo(tetrahydro-2-isobutyl-4-methyl-4(2H)-pyranol), damascone alpha, benzyl acetate, ethylvanillin, ethyl 2-methyl-pentanoate, isopropyl myristate, C10 aldehyde, rose oxide, hexylcinnamic aldehyde, hexyl salicylate, (1'R,E)-2-ethyl-4-(2,2,3-trimethyl-3'-cyclopenten-1'-yl)-2-buten-1-ol and mixtures thereof.

One aspect presented herein provides a method for treating, masking, eliminating, preventing, or reducing body malodour of a subject in need thereof, the method comprising applying to the subject's skin, a composition according to some aspects presented herein.

In one aspect, the method further treats, eliminates, prevents, or reduces perspiration of a subject in need thereof.

DETAILED DESCRIPTION

Figure 1:
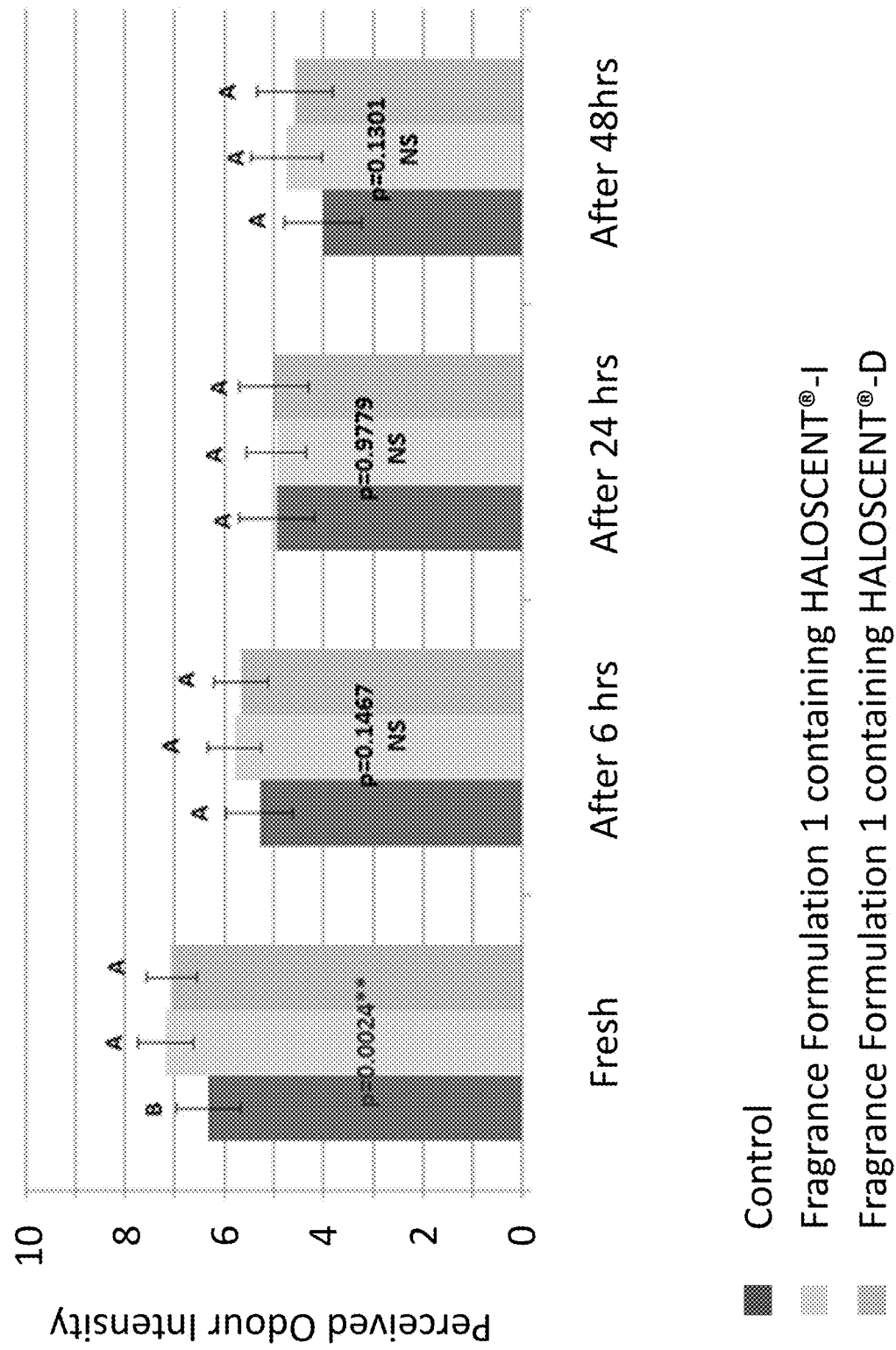
FIG. 1 shows the average perceived intensity of a spray deodorant formulation according to some aspects presented herein, compared to a control formulation.
Figure 2:
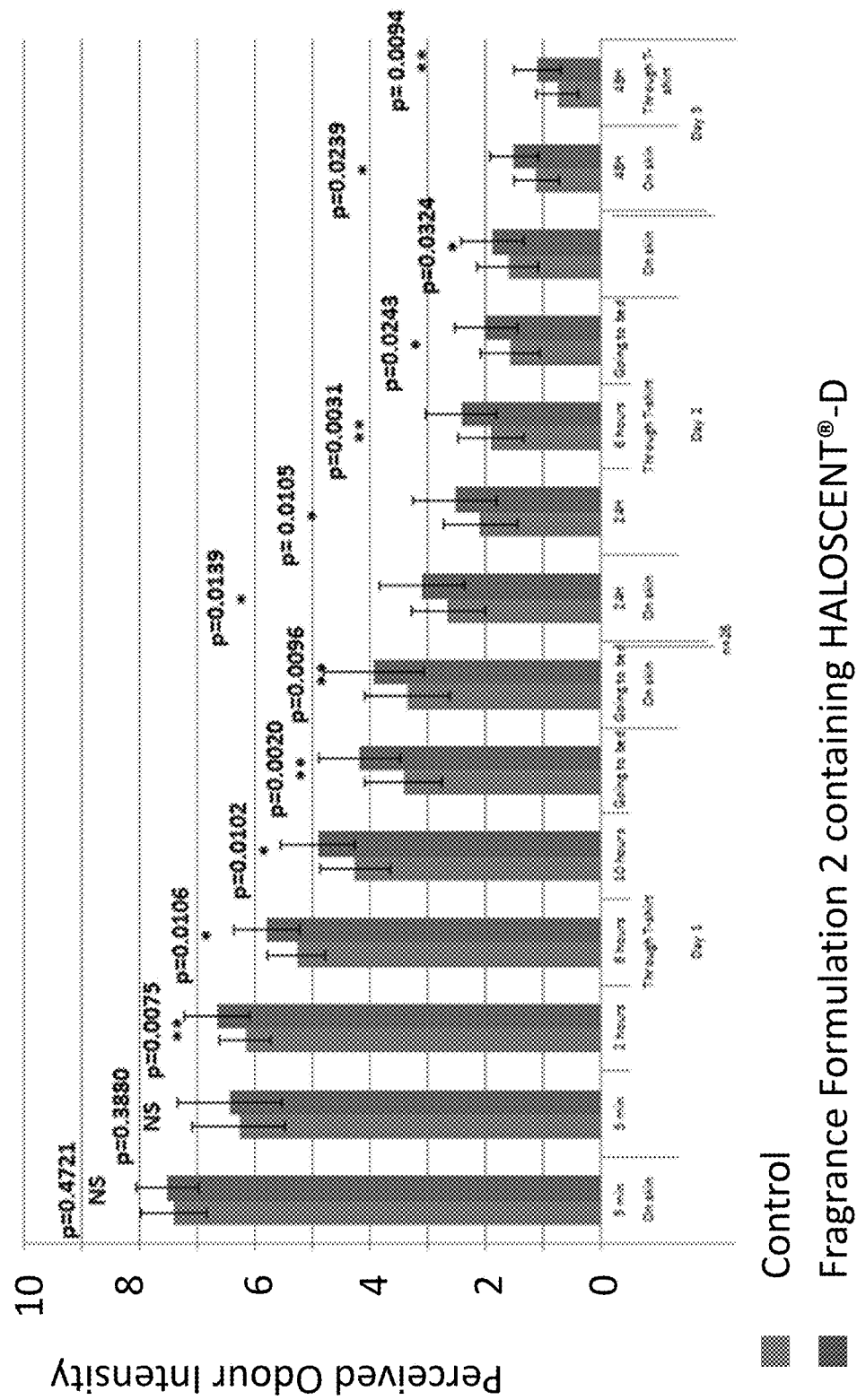
FIG. 2 shows the average perceived intensity of a spray deodorant formulation according to some aspects presented herein, after being applied to skin, compared to a control formulation, at the times indicated.
Figure 3:
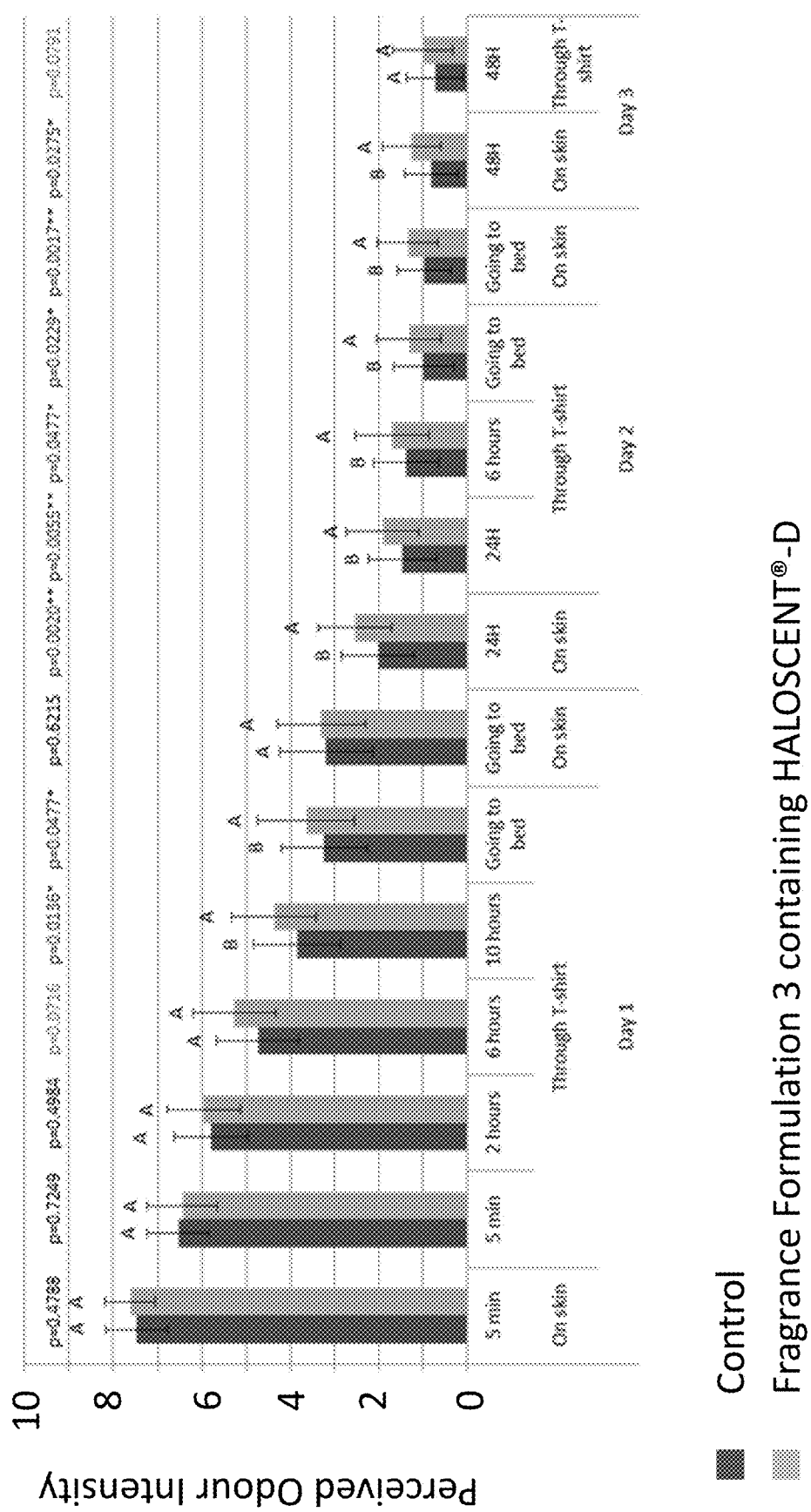
FIG. 3 shows the average perceived intensity of a spray deodorant formulation according to some aspects presented herein, after being applied to skin, compared to a control formulation, at the times indicated.
Figure 4:
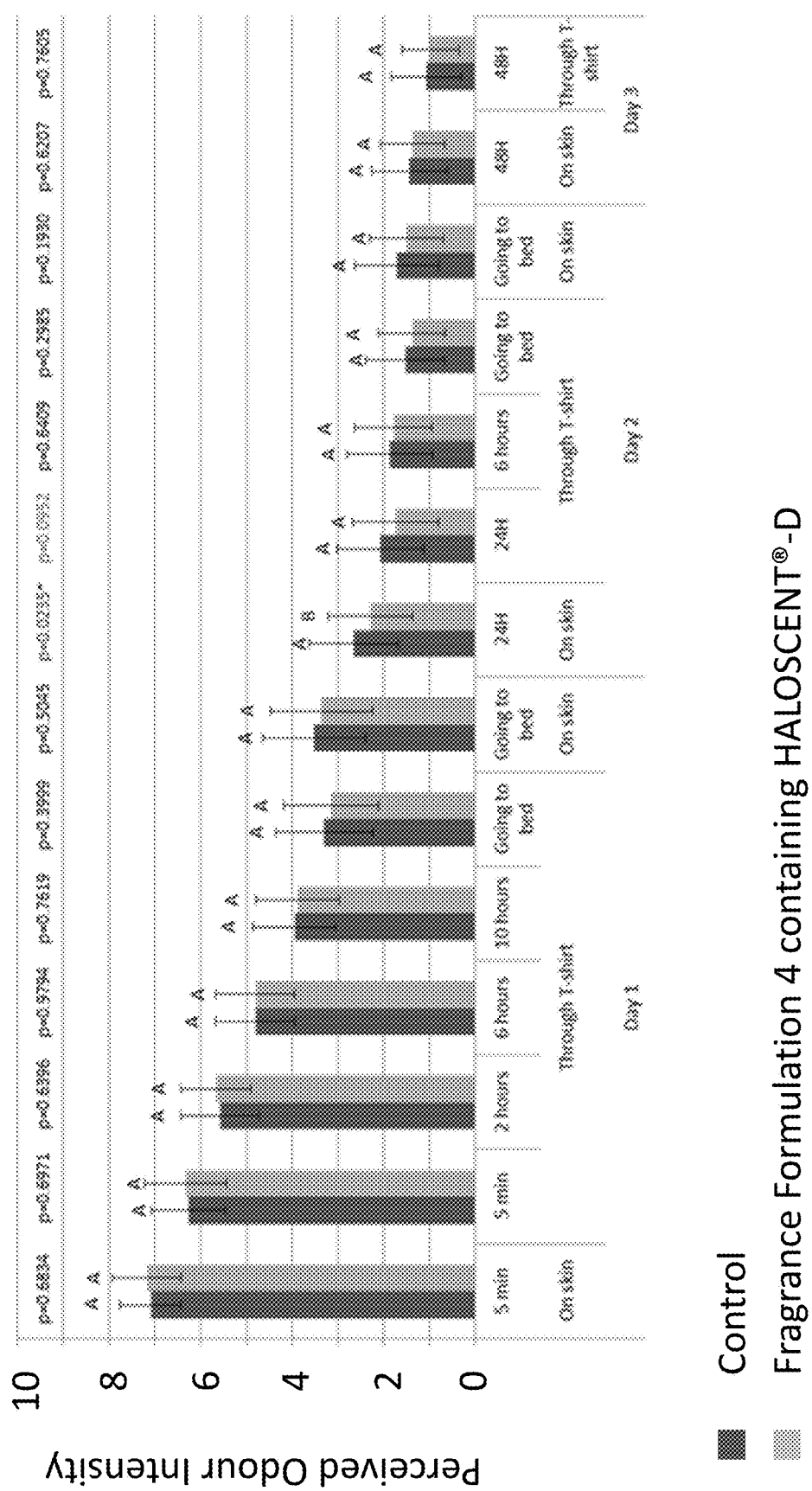
FIG. 4 shows the average perceived intensity of a spray deodorant formulation according to some aspects presented herein, after being applied to skin, compared to a control formulation, at the times indicated.
Figure 5:
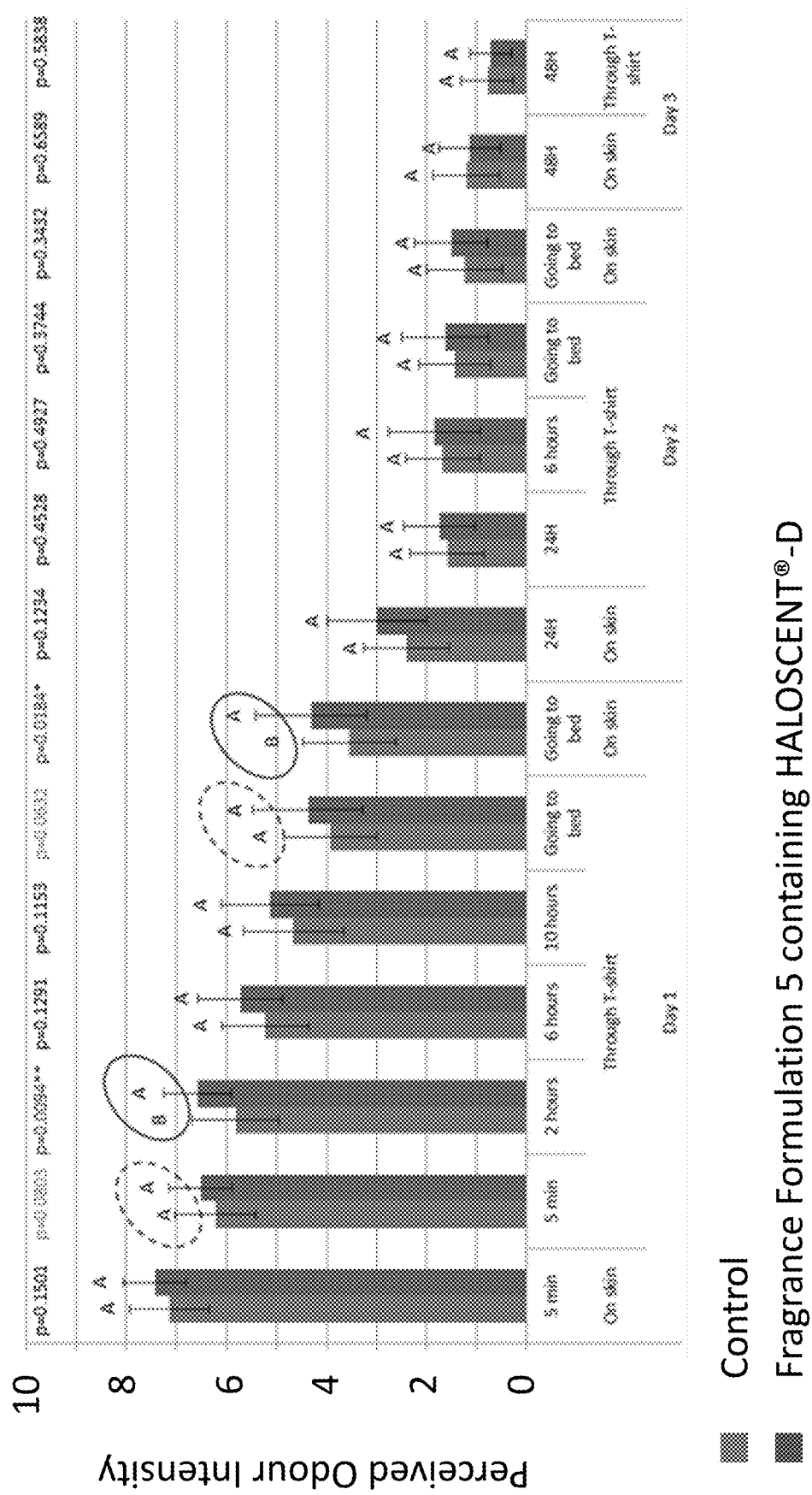
FIG. 5 shows the average perceived intensity of a spray deodorant formulation according to some aspects presented herein, after being applied to skin, compared to a control formulation, at the times indicated.
Figure 6:
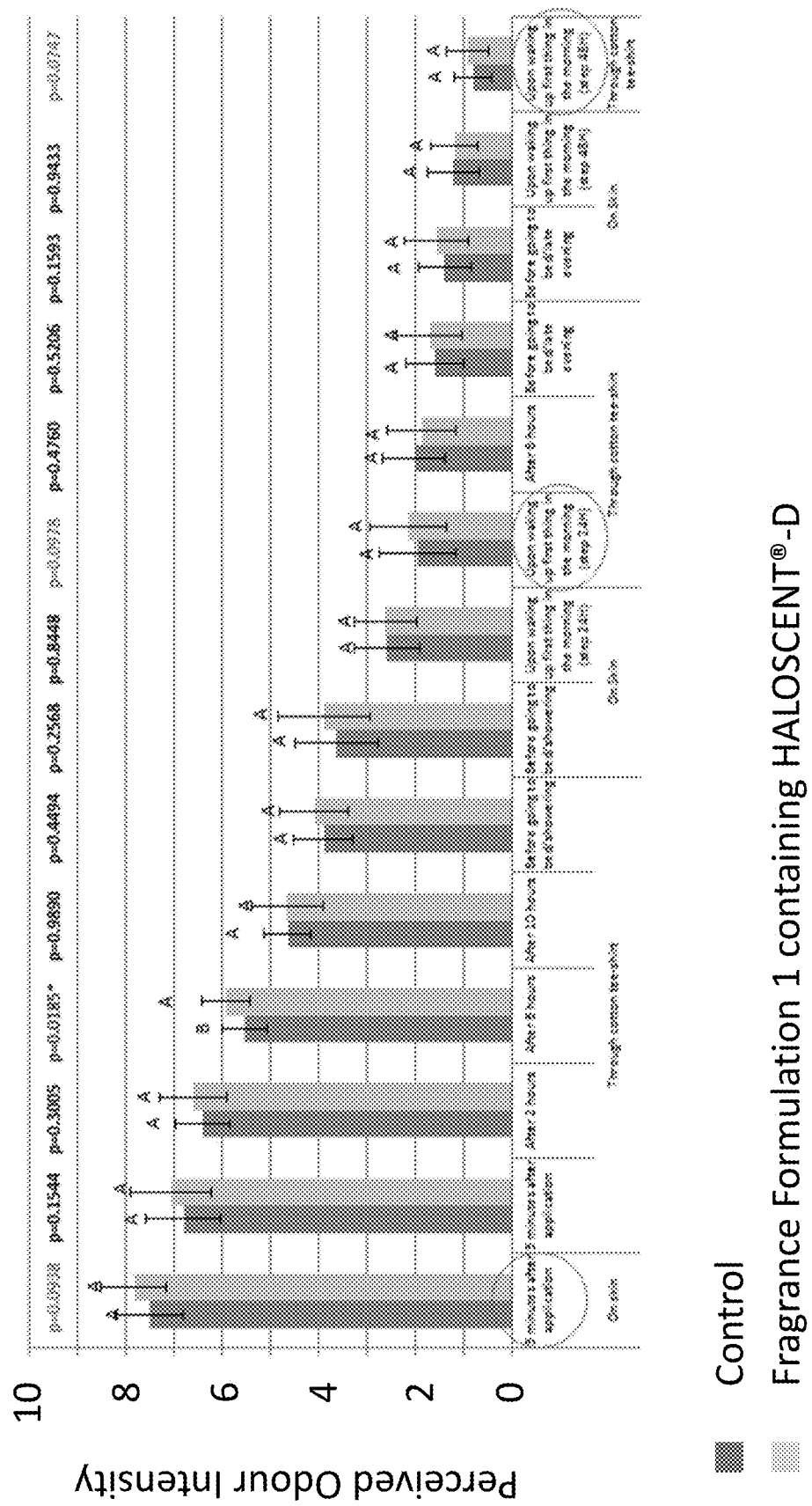
FIG. 6 shows the average perceived intensity of a spray deodorant formulation according to some aspects presented herein, after being applied to skin, compared to a control formulation, at the times indicated.
Figure 7:
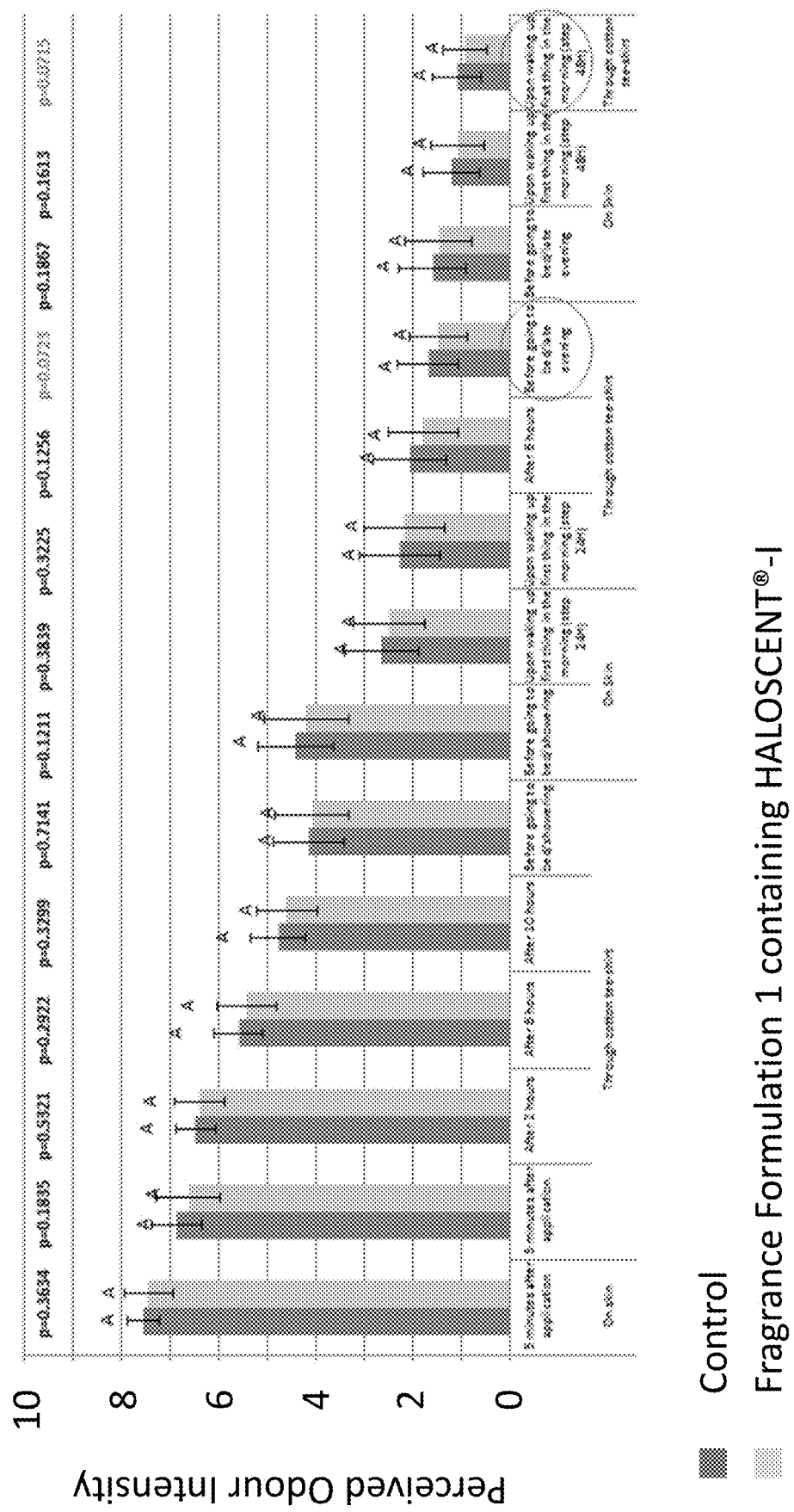
FIG. 7 shows the average perceived intensity of a spray deodorant formulation according to some aspects presented herein, after being applied to skin, compared to a control formulation, at the times indicated.
Figure 8:
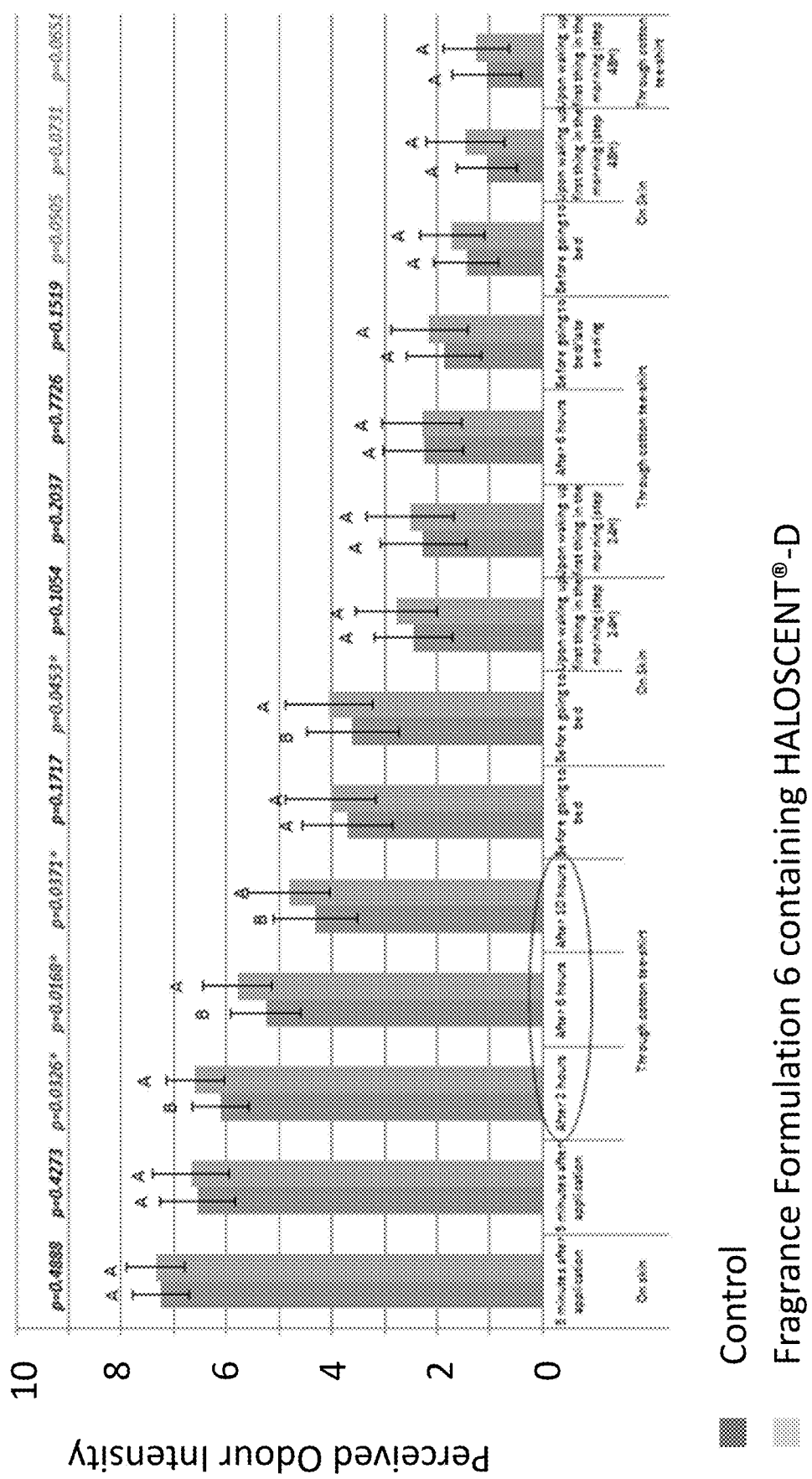
FIG. 8 shows the average perceived intensity of a spray deodorant formulation according to some aspects presented herein, after being applied to skin, compared to a control formulation, at the times indicated.
Figure 9:
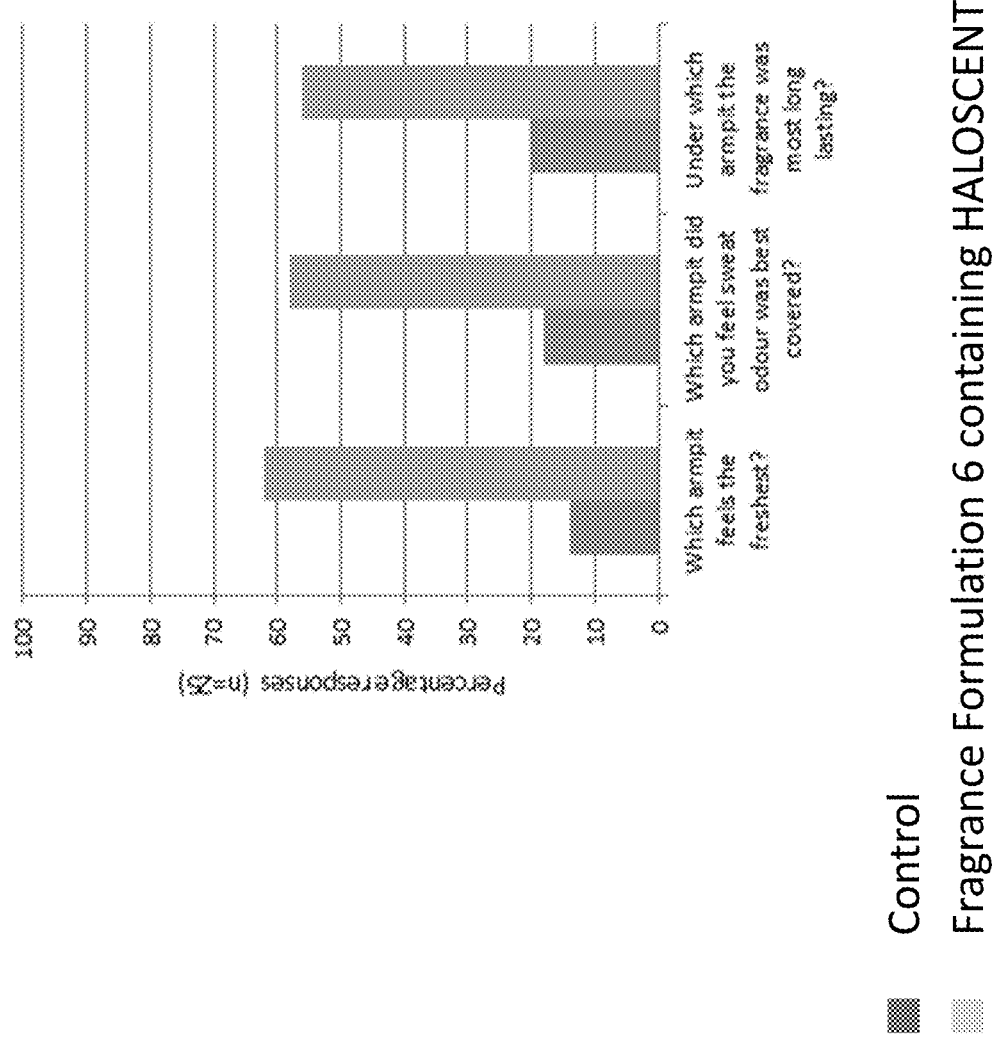
FIG. 9 shows the results of forced choice questions of a spray deodorant formulation according to some aspects presented herein, after being applied to skin, compared to a control formulation.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Some aspects presented herein provide a composition comprising:
a. a carrier;
b. a perfuming composition, comprising:
  i. at least one β-thio carbonyl derivative profragrance of formula $$P \sim\!\!\sim S - R \quad (I)$$

wherein the wavy line indicates the location of the bond between said P and the sulfur atom,
P represents a group of the formulae (P-1) to (P-9), in the form of any one of their isomers:

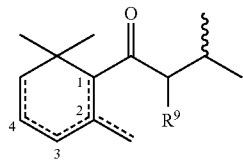
(P-1)

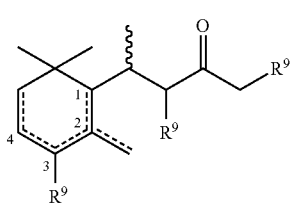
(P-2)

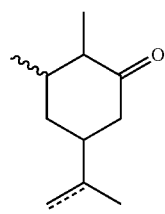
(P-3)

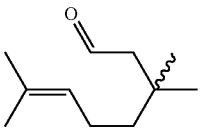
(P-4)

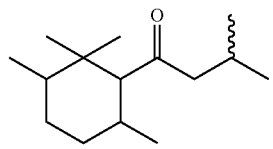
(P-5)

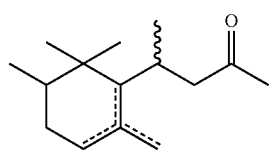
(P-6)

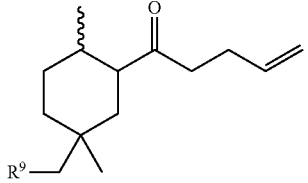
(P-7)

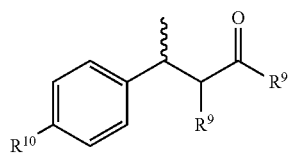
(P-8)

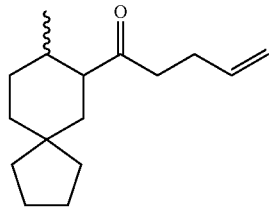
(P-9)

in which formulae the wavy lines have the meaning indicated above and the dotted lines represent a single or double bond,
$R^9$ being a hydrogen atom or a methyl group; $R^{10}$ representing a hydrogen atom, a hydroxy or methoxy group or a C1-C4 linear or branched alkyl group, and
R represents a linear or branched alkyl group having from 8 to 15 carbon atoms, optionally comprising a carboxylic functional group which is not directly linked to the sulphur atom; and
ii. a free perfume,
wherein the at least one β-thio carbonyl derivative profragrance of formula (I) is present in an amount from 0.001 to 10 wt %, relative to the total weight of the composition, and
wherein the free perfume is present in an amount from 0.0001 to 6 wt %, relative to the total weight of the composition.

In some aspects, the β-thio carbonyl derivative profragrance of formula (I) is a derivative wherein P is a group of the formulae (P-1), (P-2), (P-5) or (P-6), as defined above. In some aspects, P can be a group of the formulae (P-1) or (P-2), wherein $R^9$ represents a hydrogen atom.

In some aspects, R represents a linear alkyl group having from 8 to 15 carbon atoms, optionally comprising a carboxylic functional group which is not directly linked to the sulphur atom. In some aspects, R can be a linear alkyl group having from 10 to 14 carbon atoms. In some aspects, R is a n-dodecyl group. In some aspects, R can be a linear alkyl group having from 2 to 4 carbon atoms.

Non-limiting examples of a β-thio carbonyl profragrance derivative of formula (I) include the following: 3-(dodecylthio)-1-(2,6,6-trimethylcyclohex-3-en-1-yl)butan-1-one (derived from δ-damascone, also known and referred to herein as Haloscent® D, trademark and origin: Firmenich SA) or 3-(dodecylthio)-1-(2,6,6-trimethylcyclohex-2-en-1-yl)butan-1-one (derived from α-damascone) or 4-(dodecylthio)-4-(2,6,6-trimethylcyclohex-2-en-1-yl)butan-2-one (derived from ionone, also known and referred to herein as Haloscent® I, trademark and origin: Firmenich SA), mixtures thereof.

Another example of a β-thio carbonyl profragrance derivative of formula (I) suitable for use in the present disclosure include the β-thio carbonyl profragrance derivatives disclosed in International Patent Application Publication No. WO2013/139766.

Another example of a β-thio carbonyl profragrance derivative of formula (I) suitable for use in the present disclosure include the β-thio carbonyl profragrance derivatives disclosed in International Patent Application Publication No. WO2013/032885.

Referring to Example 2 and without intending to be limited to any particular theory, the performance of an antiperspirant and/or deodorant product can be improved by the addition of at least one β-thio carbonyl derivative profragrance of formula (I).

The improvement of performance of the antiperspirant and/or deodorant product may be, for example, elimination of body malodour, an increase feeling of freshness, reduced skin irritation, an increased perceived intensity of the fragrance of the perfume, an increased duration of the perception of the fragrance of the perfume, or any combination thereof.

Without intending to be limited to any particular theory, the elimination of body malodour may be by the prevention, reduction, or inhibition of perspiration. Alternatively, the elimination of body malodour may be by inhibiting the growth of bacteria that are responsible for the production of body malodour.

In some aspects, the at least one β-thio carbonyl derivative profragrance of formula (I) is present in an amount from 0.001 to 10 wt %, relative to the total weight of the composition.

In some aspects, the at least one β-thio carbonyl derivative profragrance of formula (I) is present at 0.001, or 0.0015, or 0.002, or 0.0025, or 0.003, or 0.0035, or 0.004, or 0.0045, or 0.005, or 0.0055, or 0.006, or 0.0065, or 0.007, or 0.0075, or 0.008, or 0.0085, or 0.009, or 0.0095, or 0.01, or 0.015, or 0.02, or 0.025, or 0.03, or 0.035, or 0.04, or 0.045, or 0.05, or 0.055, or 0.06, or 0.065, or 0.07, or 0.075, or 0.08, or 0.085, or 0.09, or 0.095, or 0.1, or 0.15, or 0.2, or 0.25, or 0.3, or 0.35, or 0.4, or 0.45, or 0.5, or 0.55, or 0.6, or 0.65, or 0.7, or 0.75, or 0.8, or 0.95, or 1.0, or 1.5, or 2.0, or 2.5, or 3.0, or 3.5, or 4.0, or 4.5, or 5.0, or 5.5, or 6.0, or 6.5, or 7.0, or 7.5, or 8.0, or 8.5, or 9.0, or 10 wt %, relative to the total weight of the composition.

In some aspects, the at least one β-thio carbonyl derivative profragrance of formula (I) is present in an amount from 0.001 to 7 wt %, relative to the total weight of the composition.

In some aspects, the at least one β-thio carbonyl derivative profragrance of formula (I) is present in an amount from 0.001 to 5 wt %, relative to the total weight of the composition.

In some aspects, the at least one β-thio carbonyl derivative profragrance of formula (I) is present in an amount from 0.001 to 0.1 wt %, relative to the total weight of the composition.

In some aspects, the at least one β-thio carbonyl derivative profragrance of formula (I) is present in an amount from 0.001 to 0.02 wt %, relative to the total weight of the composition.

Free Perfume: As used herein, the term "perfume", or "free perfume", or "encapsulated perfume" refers to a compound or mixture of perfuming ingredients, which are used in a perfuming preparation or composition to impart a hedonic effect. In other words such perfuming ingredients, to be considered as being a perfuming one, must be recognized by a person skilled in the art as being able to impart or modify in a positive or pleasant way the odour of a composition, and not just as having an odour.

As used herein, the term "perfuming ingredient" it is meant a compound, which is used for the primary purpose of conferring or modulating an odour. In other words such an ingredient, to be considered as being a perfuming one, must be recognized by a person skilled in the art as being able to at least impart or modify in a positive or pleasant way the odour of a composition, and not just as having an odour. For the purpose of the present disclosure, perfume accord also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odour, such as long-lasting, blooming, malodour counteraction, antimicrobial effect, microbial stability, insect control.

The nature and type of the perfuming ingredients do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. In some embodiments, the solvent is not an alcohol. Examples of such solvents are diethyl phthalate, isopropyl myristate, Abalyn® (rosin resins, available from Eastman), benzyl benzoate, ethyl citrate, limonene or other terpenes, or isoparaffins. In some aspects, the solvent is very hydrophobic and highly sterically hindered, like for example Abalyn® or benzyl benzoate.

According to any one of the above aspects, the free perfume is present in an amount from 0.0001 to 10 wt %, relative to the total weight of the composition. In some aspects, the free perfume is present in an amount from 0.0001 to 9 wt %, relative to the total weight of the composition. In some aspects, the free perfume is present in an amount from 0.0001 to 8 wt %, relative to the total weight of the composition. In some aspects, the free perfume is present in an amount from 0.0001 to 7 wt %, relative to the total weight of the composition. In some aspects, the free perfume is present in an amount from 0.0001 to 6 wt %, relative to the total weight of the composition. In some aspects, the free perfume is present in an amount from 0.0001 to 5 wt %, relative to the total weight of the composition. In some aspects, the free perfume is present in an amount from 0.0001 to 4 wt %, relative to the total weight of the composition. In some aspects, the free perfume is present in an amount from 0.0001 to 3 wt %, relative to the total weight of the composition. In some aspects, the free perfume is present in an amount from 0.0001 to 2 wt %, relative to the total weight of the composition. In some aspects, the free perfume is present in an amount from 0.0001 to 1 wt %, relative to the total weight of the composition.

In some aspects, the free perfume is present in an amount from 0.0001 to 0.4 wt %, relative to the total weight of the composition.

In some aspects, the free perfume is present at 0.0001, or 0.00015, or 0.0002, or 0.00025, or 0.0003, or 0.00035, or 0.0004, or 0.00045, or 0.0005, or 0.00055, or 0.0006, or 0.00065, or 0.0007, or 0.00075, or 0.0008, or 0.00085, or 0.0009, or 0.00095, or 0.001, or 0.0015, or 0.002, or 0.0025, or 0.003, or 0.0035, or 0.004, or 0.0045, or 0.005, or 0.0055, or 0.006, or 0.0065, or 0.007, or 0.0075, or 0.008, or 0.0085, or 0.009, or 0.0095, or 0.01, or 0.015, or 0.02, or 0.025, or 0.03, or 0.035, or 0.04, or 0.045, or 0.05, or 0.055, or 0.06, or 0.065, or 0.07, or 0.075, or 0.08, or 0.085, or 0.09, or 0.095, or 0.1, or 0.15, or 0.2, or 0.25, or 0.3, or 0.35, or 0.4, or 0.45, or 0.5, or 0.55, or 0.6, or 0.65, or 0.7, or 0.75, or 0.8, or 0.95, or 1.0, or 1.1, or 1.15, or 1.2, or 1.25, or 1.3, or 1.35, or 1.4, or 1.45, or 1.5, or 1.55, or 1.6, or 1.65, or 1.7, or 1.75, or 1.8, or 1.95, or 2.0, or 2.1, or 2.15, or 2.2, or 2.25, or 2.3, or 2.35, or 2.4, or 2.45, or 2.5, or 2.55, or 2.6, or 2.65, or 2.7, or 2.75, or 2.8, or 2.95, or 3.0, or 3.1, or 3.15, or 3.2, or 3.25, or 3.3, or 3.35, or 3.4, or 3.45, or 3.5, or 3.55, or 3.6, or 3.65, or 3.7, or 3.75, or 3.8, or 3.95, or 4.0, or 4.1, or 4.15, or 4.2, or 4.25, or 4.3, or 4.35, or 4.4, or 4.45, or 4.5, or 4.55, or 4.6, or 4.65, or 4.7, or 4.75, or 4.8, or 4.95, or 5.0, or 5.1, or 5.15, or 5.2, or 5.25, or 5.3, or 5.35, or 5.4, or 5.45, or 5.5, or 5.55, or 5.6, or 5.65, or 5.7, or 5.75, or 5.8, or 5.95, or 6.0 wt %, relative to the total weight of the composition.

In some aspects, the free perfume is selected from the group consisting of: geraniol, citronellol, dihydromyrcenol, hydroxycitronellal, 3-Methyl-5-cyclopentadecen-1-one, cyclopentadecanone, (1S,1'R)-[1-(3,3-Dimethyl-1-cyclohexyl)ethoxycarbonyl]methyl propanoate, pentadecenolide, 7-Methyl-2H,4H-1,5-benzodioxepin-3-one, indole, 3-methyl-4-(2,6,6-trimethyl-2-cyclohexen-1-yl)-3-buten-2-one (isoraldeine), 1-(5,5-dimethylcyclohex-1-en-1-yl)pent-4-en-1-one, amyl salicyclate, methyl dihydrojasmonate, cyclohexyl salicylate and mixtures thereof.

In some aspects, the free perfume comprises perfuming ingredients selected from the group consisting of: geraniol, citronellol, dihydromyrcenol, hydroxycitronellal, 3-Methyl-5-cyclopentadecen-1-one, cyclopentadecanone, (1S,1'R)-[1-(3,3-Dimethyl-1'-cyclohexyl)ethoxycarbonyl]methyl propanoate, pentadecenolide, 7-Methyl-2H,4H-1,5-benzodioxepin-3-one, indole, 3-methyl-4-(2,6,6-trimethyl-2-cyclohexen-1-yl)-3-buten-2-one 1-(5,5-dimethylcyclohex-1-en-1-yl)pent-4-en-1-one, amyl salicyclate, methyl dihydrojasmonate and cyclohexyl salicylate in an amount comprised between 0.0001 wt % and 0.4 wt %, relative to the total weight of the composition.

In some aspects, the free perfume comprises at least one perfuming ingredient selected from the group consisting of: Iso E Super (1-(octahydro-2,3,8,8-tetramethyl-2-naphtalenyl)-1-ethanone; origin: International Flavors & Fragrances), dipropylene glycol, 2,4-Dimethyl-3-cyclohexene-1-carbaldehyde, Cetalox® (dodecahydro-3a,6,6,9a-tetramethyl-naphtho[2,1-b]furan; trademark and origin: Firmenich SA), linalool, coumarin, (Z)-3-hexen-1-ol, allyl amyl glycolate, Verdox® (2-tert-butyl-1-cyclohexyl acetate; trademark and origin: International Flavors & Fragrances), styrallyl acetate, Lilial® (3-(4-tert-butylphenyl)-2-methylpropanal; trademark and origin: Givaudan SA), 1,4-dioxa-5,17-cycloheptadecanedione, crystal moss, gamma undecalactone, (Z)-hex-3-en-1-yl acetate, Florol® (neo(tetrahydro-2-isobutyl-4-methyl-4(2H)-pyranol); trademark and origin: Firmenich SA), damascone alpha, benzyl acetate, ethylvanillin, ethyl-2-methyl-pentanoate, isopropyl myristate, C10 aldehyde, rose oxide, hexylcinnamic aldehyde, hexyl salicylate, Dartanol® ((1'R,E)-2-ethyl-4-(2',2',3'-trimethyl-3'-cyclopenten-1'-yl)-2-buten-1-ol; trademark and origin: Firmenich SA).

Antiperspirant or Deodorant Products:

The compositions presented herein may be incorporated into any antiperspirant or deodorant product. Exemplary products include wax-based sticks, soap-based sticks, compressed powder sticks, roll-on suspensions or solutions, emulsions, gels, creams, squeeze sprays, pump sprays, aerosols, and the like. Each product form may contain its own selection of additional components, some essential and some optional. The types of components typical for each of the above product forms may be incorporated in the corresponding compositions presented herein.

As used herein, the term "antiperspirant or deodorant product" refers to the normal meaning in the art; i.e. a composition applied on skin allowing to reduce or prevent body odour.

Depending of the type of product, the deodorant or antiperspirant product may comprise supplementary ingredients enabling to obtain the desired form. Non-limiting examples of suitable ingredients include emollient(s), solubilizer(s), deodorant active(s), antioxidant(s), preservative(s), carrier(s), odour entrapper(s), propellant(s), primary structurant(s), antiperspirant active(s), additional chassis ingredient(s), volatile silicone solvent(s), gellant(s), buffering agent and residue masking material(s). A person skilled in the art is able to select them on the basis of its general knowledge and according to intended form of the deodorant or antiperspirant composition.

For example, by way of illustration, a roll-on deodorant or antiperspirant product may comprise water, emollient, solubilizer, deodorant or antiperspirant actives, antioxidants, preservatives, or combinations thereof; a clear gel product or antiperspirant product may comprise water, emollient, solubilizer, deodorant or antiperspirant actives, antioxidants, preservatives, ethanol, or combinations thereof a body spray may contain a carrier, deodorant or antiperspirant actives, odour entrappers, propellant, or combinations thereof; an invisible solid deodorant or antiperspirant product may contain a primary structurant, deodorant or antiperspirant actives, and additional chassis ingredient(s); a soft solid deodorant or antiperspirant product may comprise volatile silicone, deodorant or antiperspirant actives, gellant, residue masking material, or combinations thereof an aerosol deodorant or antiperspirant product may comprise a carrier, a propellant, or a combination thereof.

Emollients suitable for deodorant or antiperspirant products include, but are not limited to, propylene glycol, polypropylene glycol (like dipropylene glycol, tripropylene glycol, etc.), diethylene glycol, triethylene glycol, neopentyl glycol diheptanoate, PEG-4, PEG-8, 1,2-pentanediol, 1,2-hexanediol, hexylene glycol, glycerin, C2 to C20 monohydric alcohols, C2 to C40 dihydric or polyhydric alcohols, alkyl ethers of polyhydric and monohydric alcohols, dicaprylyl carbonate, dicaprylyl ether, diethylhexylcyclohexane, dibutyl adipate, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Suitable deodorant actives can include any topical material that is known or otherwise effective in preventing or eliminating malodour, including malodour associated with sweat and/or perspiration. Suitable deodorant actives may be selected from the group consisting of antimicrobial agents (e.g., bacteriocides, fungicides), malodour-absorbing material, and combinations thereof.

Antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Suitable odour entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, including alpha-cyclodextrin, beta-cyclodextrin, gamma-cyclodextrin and/or their derivatives and/or mixtures thereof.

A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof. Suitable solubilizers include, for example, polyethylene glycol ether of Cetearyl Alcohol, hydrogenated castor oil such as polyoxyethylene hydrogenated castor oil, polyoxyethylene 2 stearyl ether, polyoxyethylene 20 stearyl ether, and combinations thereof.

Suitable preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathan® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N, N'-bis(hydroxy-methyl) urea, commonly known as diazolidinyl urea, available under the trade name Germall® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, German 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

Suitable carriers can include, water, alcohol, or combinations thereof. Useful alcohols include $C_1$-$C_3$ alcohols. In some aspects, the alcohol is ethanol.

Some examples of propellants include compressed air, nitrogen, inert gases, carbon dioxide, and mixtures thereof. Propellants may also include gaseous hydrocarbons like propane, n-butane, isobutene, cyclopropane, and mixtures thereof; e.g. A-46 (a mixture of isobutane, butane and propane), A-31 (isobutane), A-17 (n-butane), A-108 (propane), AP70 (a mixture of propane, isobutane and nbutane), AP40 (a mixture of propane, isobutene and n-butane), AP30 (a mixture of propane, isobutane and n-butane). Some non-limiting examples of propellants include 1,1-difluoroethane, 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2, 2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof.

The term "primary structurant" as used herein means any material known or otherwise effective in providing suspending, gelling, viscosifying, solidifying, and/or thickening properties to the composition or which otherwise provide structure to the final product form. These primary structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof. Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Antiperspirant actives may include astringent metallic salts, especially inorganic and organic salts of aluminum, zirconium and zinc, as well as mixtures thereof. Even more specifically, antiperspirant actives may be selected from the group consisting of aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY and aluminum zirconium trichlorohydrate GLY.

Chassis ingredients may be an additional structurant such as stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof; non-volatile organic fluids such as mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate or isobutyl stearate; clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Volatile silicone solvents suitable for use in the antiperspirant compositions include, but are not limited to, solvent such as Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

The gellant material may comprise saturated or unsaturated, substituted or unsubstituted, fatty alcohols or mixtures of fatty alcohols having from about 20 to about 60 carbons atoms, alternatively from about 20 to about 40 carbon atoms. In some embodiments, the gallant materials comprise combinations of the fatty alcohols. In some embodiments, the fatty alcohol gellants are may be saturated, unsubstituted monohydric alcohols or combinations thereof, which have a melting point of at less than about 110° C., alternatively from about 60° to about 110° C., alternatively between about 100° C. and 110° C.

Specific examples of fatty alcohol gellants for use in the antiperspirant products that are commercially available include, but are not limited to, Unilin® 425, Unilin® 350, Unilin® 550 and Unilin® 700 (supplied by Petrolite).

A suitable buffering agent may be alkaline, acidic or neutral. The buffer may be used in the composition or product for maintaining the desired pH. Suitable buffering agents include, for example, hydrochloric acid, sodium hydroxide, potassium hydroxide, and combinations thereof.

Non-limiting examples of suitable residue masking materials for use in the antiperspirant products include butyl stearate, diisopropyl adipate, petrolatum, nonvolatile silicones, octyldodecanol, phenyl trimethicone, isopropyl myristate, $C_{12-15}$ ethanol benzoates and PPG-14 Butyl Ether.

The deodorant or antiperspirant products disclosed herein may comprise other optional ingredients such as emulsifiers, distributing agents, antimicrobials, pharmaceutical or other topical actives, surfactants, and the like.

The nature, amount and type of ingredients does not warrant a more detailed description here, which in any case would not be exhaustive, the skilled person being able to select them on the basis of its general knowledge and according to intended form.

In some aspects, the composition comprises less than 95 wt % of water, relative to the total weight of the composition. In some aspects, the composition comprises less than 90 wt % of water, relative to the total weight of the composition. In some aspects, the composition comprises less than 85 wt % of water, relative to the total weight of the composition. In some aspects, the composition comprises less than 80 wt % of water, relative to the total weight of the composition. In some aspects, the composition comprises less than 75 wt % of water, relative to the total weight of the composition. In some aspects, the composition comprises less than 70 wt % of water, relative to the total weight of the composition. In some aspects, the composition comprises less than 65 wt % of water, relative to the total weight of the composition. In some aspects, the composition comprises less than 60 wt % of water, relative to the total weight of the composition. In some aspects, the composition comprises less than 55 wt % of water, relative to the total weight of the composition. In some aspects, the composition comprises less than 50 wt %, or less than 40 wt %, or less than 30 wt %, or less than 20 wt %, or less than 10 wt % of water, relative to the total weight of the deodorant or antiperspirant composition. In some aspects, the composition is water-free.

The present invention is best illustrated but is not limited to the following examples.

EXAMPLES

Example 1

Assessment of Coloration of a Deodorant Formulation According to Some Aspects Presented Herein Preparation of an Antiperspirant Spray Formulation: Using a high speed stirrer, Silica (Table 1) and Quaternium-18-Hectorite (Table 1) were added to the Isopropyl miristate (Table 1) and Cyclomethicone mixture (Table 1). Once completely swollen, Aluminium Chlorohydrate (Table 1) was added portion wise under stirring until the mixture was homogeneous and without lumps. The aerosol cans were filled with 25% Suspension of the suspension and 75% of Propane/Butane (2.5 bar).

TABLE 1

Antiperspirant spray formulation

| Ingredient | Amount (wt %) |
| --- | --- |
| Cyclomethicone[1] | 53.51 |
| Isopropyl miristate | 9.04 |
| Silica[2] | 1.03 |
| Quaternium-18-Hectorite[3] | 3.36 |
| Aluminium Chlorohydrate[4] | 33.06 |

[1] Dow Corning ® 345 Fluid; trademark and origin: Dow Corning
[2] Aerosil ® 200; trademark and origin: Evonik
[3] Bentone ® 38; trademark and origin: Elementis Specialities
[4] Micro Dry Ultrafine; origin: Reheis Preparation of Deodorant Spray Formulation: All the ingredients according to the sequence of the Table 2 were mixed and dissolved. Then the aerosol cans were filled, crimp and add the propellant (Aerosol filling: 40% active solution 60% Propane/Butane 2.5 bar).

TABLE 2

Deodorant spray formulation

| Ingredient | Amount (wt %) |
| --- | --- |
| Ethanol 95% | 90.65 |
| Triclosan[1] | 0.26 |
| Isopropyl miristate | 9.09 |

[1] Irgasan ® DP 300; trademark and origin: BASF a) Preparation of a Deodorant Roll-On Formulation Part A was prepared by sprinkling little by little the Hydroxyethylcellulose (Table 3) in the water (Table 3) whilst rapidly stirring with the turbine. Stirring was continued until the Hydroxyethylcellulose had entirely swollen and giving a limpid gel. Then, Part B (Table 3) was poured little by little in Part A whilst continuing stirring until the whole was homogeneous. Part C was added (Table 3).

TABLE 3

Deodorant roll-on formulation

| Ingredient | Amount (wt %) |
| --- | --- |
| Water (Part A) | 50.51 |
| Hydroxyethylcellulose[1] (Part A) | 0.71 |
| Ethanol 95% (Part B) | 40.40 |
| 1,2-Propylene Glycol (Part B) | 5.05 |
| Triclosan[2] (Part B) | 0.30 |
| PEG-40 Hydrogenated castor oil[3] (Part C) | 3.03 |

[1] Natrosol ® 250 H; trademark and origin: Ashland
[2] Irgasan ® DP 300; trademark and origin: BASF
[3] Cremophor ® RH 40; trademark and origin: BASF Preparation of a Deodorant Stick Formulation: All the components of Part A were weighted (Table 4) and heated up to 70-75° C. Ceteareth-25 (Table 4) was added once the other Part A ingredients were mixed and heated. Once the Ceteareth-25 was dissolved, the Stearic Acid was added. Part B was prepared by dissolving the Triclosan (Table 4) in 1,2 Propylene Glycol (Table 4). Water which has evaporated was added. Slowly under mixing, Part B was poured into part A. To stock, a plastic bag into the bucket was put in to be sealed after cooling. Moulds was filled at about 70° C.

TABLE 4

Deodorant stick formulation

| Ingredient | Amount (wt %) |
| --- | --- |
| Stearic acid (Part A) | 5.05 |
| 1,2-propylene glycol (Part A) | 41.87 |
| Sodium hydroxide 20% aqueous solution (Part A) | 4.24 |
| Water (Part A) | 30.30 |
| Tetrasodium EDTA[1] (Part A) | 0.10 |
| Ceteareth-25[2] (Part A) | 1.52 |
| PPG-3 Myristyl ether[3] (Part A) | 1.52 |
| 1,2-propylene glycol (Part B) | 15.14 |
| Triclosan[4] (Part B) | 0.25 |

[1] Edeta ® B Power; trademark and origin: BASF
[2] Cremophor ® A25; trademark and origin: BASF
[3] Tegosoft ® APM; trademark and origin: Evonik
[4] Irgasan ® DP 300; trademark and origin: BASF Preparation of an Antiperspirant Stick Formulation: All the components of Part A were weighted (Table 5), heated up to 70-75° C. and mixed well. Ingredient of Part B was dispersed in Part A. The mixture was mixed and putted into a tick at 65° C.

TABLE 5

Antiperspirant stick formulation

| Ingredient | Amount (wt %) |
| --- | --- |
| Cyclomethicone[1] (Part A) | 55.56 |
| Stearyl Alcohol[2] (Part A) | 21.21 |
| PPG-14 Butyl ether[3] (Part A) | 2.02 |
| Hydrogenated Castor Oil[4] (Part A) | 1.01 |
| Aluminium Zirconium tetrachlorohydrex-Gly[5] (Part B) | 20.20 |

[1] Dow Corning ® 345 Fluid; trademark and origin: Dow Corning
[2] Lanette ® 18; trademark and origin: BASF
[3] Tegosoft ® PBE; trademark and origin: Evonik
[4] Cutina ® HR; trademark and origin: BASF
[5] Summit AZP-908; trademark and origin: Reheis Assessment of Coloration in the Perfuming Ingredients: To set of deodorant or antiperspirant formulations of point a) to e) has been prepared. A perfuming ingredient (0.5 wt %—Table 6, 7 and 8) was added to the first set a and a perfuming ingredient (0.5 wt %—Table 6, 7 and 8) and Haloscent® D (0.5 wt %) were added to the second set. All these formulations were placed at 3° C. and 45° C. for several weeks. All formulations were evaluated in comparison with unperfumed deodorant or antiperspirant formulation. The coloration of each formulation was assessed by a minimum of 2 panelists.

TABLE 6

Coloration of antiperspirant stick in function of perfuming ingredients after 7 days

| Ingredients | AP Stick 3° C. | AP Stick 45° C. | AP Stick + Haloscent ® D 3° C. | AP Stick + Haloscent ® D 45° C. |
|---|---|---|---|---|
| UNPERFUMED | VSCOYE | SCOYE | DECO PI | DECO PI |
| (E)-3,7-DIMETHYL-2,6-OCTADIEN-1-OL | DECO | NC | VSCO | NC |
| (+−)-3,7-DIMETHYL-6-OCTEN-1-OL | DECO | DECO | VSCOYE | VSCOYE |
| HABANOLIDE[1] | DECO | VSCOYE | DECO | SCOYE |
| 2,3-BENZOPYRROLE | DECO | VSCOYE | COPI | VSCOYE |
| PENTYL 2-HYDROXYBENZOATE | VSCOPI | NC | VSCOPI | VSCOPI |

CO: color
COYE: yelow color
[1] 1-OXA-12-CYCLOHEXADECEN-2-ONE (A) + 1-OXA-13-CYCLOHEXADECEN-2-ONE
VSCOYE: very slight yellow color
SCOYE: slight yellow color
VCOYE: very yellow color
NC: no color
DECO: decoloration
CL: cloud
VCL: very cloud
WH: white
VCOBR: very brown color
COPI: ping color

TABLE 7

Coloration of deodorant or antperpirant spray in function of perfuming ingredients after 15 days

| Ingredients | DEO SPRAY 3° C. | DEO SPRAY 45° C. | DEO SPRAY + Haloscent ® D 3° C. | DEO SPRAY + Haloscent ® D 45° C. | AP SPRAY 3° C. | AP SPRAY 45° C. | AP SPRAY + Haloscent ® D 3° C. | AP SPRAY + Haloscent ® D 45° C. |
|---|---|---|---|---|---|---|---|---|
| UNPERFUMED | SCOYE | COYE | SCOYE | COYE | NC | NC | NC | SCOYE |
| (+−)-3,7-DIMETHYL-6-OCTEN-1-OL | NC | NC | NC | NC | NC | NC | SCOYE | SCOYE |
| (+−)-(4E)-3-METHYL-4-CYCLOPENTADECEN-1-ONE (A) + (+−)-(5E)-3-METHYL-5-CYCLOPENTADECEN-1-ONE(B) + (+−)-(5Z)-3-METHYL-5-CYCLOPENTADECEN-1-ONE (C) | NC | NC | NC | NC | NC | NC | COYE | COYE |
| (Z)-4-CYCLOPENTADECEN-1-ONE | NC | NC | COYE | COYE | NC | NC | NC | NC |
| HABANOLIDE[2] | NC | NC | DECO | DECO | NC | NC | SCOYE | SCOYE |
| 7-ISOPROPYL-2H,4H-1,5-BENZODIOXEPIN-3-ONE | CO | CO | CO | CO | COYE | SCOYE | COYE | COYE |

CO: color
COYE: yellow color
SCOYE: slight yellow color
VCOYE: very yellow color
NC: no color
DECO: discoloration
CL: cloud
VCL: very cloud
WH: white
VCOBR: very brown color
COPI: ping color
[2] 1-OXA-12-CYCLOHEXADECEN-2-ONE (A) + 1-OXA-13-CYCLOHEXADECEN-2-ONE

TABLE 8

Coloration of deodorant roll-on or stick in function of perfuming ingredients after 15 days

| Ingredients | DEO ROLL-ON 3° C. | DEO ROLL-ON 45° C. | DEO ROLL-ON + Haloscent ® D 3° C. | DEO ROLL-ON + Haloscent ® D 45° C. | DEO STICK 3° C. | DEO STICK 45° C. | DEO STICK+ Haloscent ® D 3° C. | DEO STICK+ Haloscent ® D 45° C. |
|---|---|---|---|---|---|---|---|---|
| UNPERFUMED | NC | NC | NC | NC | NC | NC | NC | COYE CL |
| (E)-3,7-DIMETHYL-2,6-OCTADIEN-1-OL | NC | NC | NC | NC | NC | NC | COYE | COYE |

TABLE 8-continued

Coloration of deodorant roll-on or stick in function of perfuming ingredients after 15 days

| Ingredients | DEO ROLL-ON 3° C. | DEO ROLL-ON 45° C. | DEO ROLL-ON + Haloscent ® D 3° C. | DEO ROLL-ON + Haloscent ® D 45° C. | DEO STICK 3° C. | DEO STICK 45° C. | DEO STICK+ Haloscent ® D 3° C. | DEO STICK+ Haloscent ® D 45° C. |
|---|---|---|---|---|---|---|---|---|
| (+−)-3,7-DIMETHYL-6-OCTEN-1-OL | NC | NC | NC | NC | NC | NC | SCOYE | NC |
| 2-METHYL-6-METHYLIDENEOCTAN-2-OL | NC | NC | NC | NC | NC | NC | SCOYE | NC |
| HYDROXYCITRONELLAL[3] | NC | NC | NC | VSCOYE | NC | NC | SCOYE | NC |
| MUSCENONE DELTA[4] | VCL | SCOYE | WH | COYE | NC | NC | NC | NC |
| EXALTENONE[5] | VCL | VCL | WH | CL | NC | NC | NC | NC |
| ROMANDOLIDE[6] | VCL | NC | VCL | COYE | NC | NC | NC | NC |
| HABANOLIDE[7] | VCL | VCL | WH | VCL | NC | NC | NC | NC |
| CALONE[8] | NC | DECO | NC | CO | COPI | VCOBR | COPI | VCOBR |
| 2,3-BENZOPYRROLE | NC | NC | NC | VSCOYE | NC | SCOYE | NC | NC |
| ISORALDEINE 70P[9] | VCL | NC | WH | COYE | NC | VCOYE | NC | VCOYE |
| DYNASCONE[10] | VCL | NC | WH | SCOYE | NC | VCOYE | SCOYE | VCOYE |
| AMYLE SALICYLATE[11] | VCL | NC | WH | VCL | NC | NC | NC | NC |

CO: color
COYE: yellow color
SCOYE: slight yellow color
VCOYE: very yellow color
NC: no color
[3](+−)-2,6-dimethyl-7-(4-methyl-1,3-dioxolan-2-yl)-2-heptanol
[4](+−)-(4E)-3-METHYL-4-CYCLOPENTADECEN-1-ONE (A) + (+−)-(5E)-3-METHYL-5-CYCLOPENTADECEN-1-ONE (B) + (+−)-(5Z)-3-METHYL-5-CYCLOPENTADECEN-1-ONE (C)
[5](Z)-4-CYCLOPENTADECEN-1-ONE
[6]2-{(1S)-1-[(1R)-3,3-dimethylcyclohexyl]ethoxy}-2-oxoethyl propionate
[7]1-OXA-12-CYCLOHEXADECEN-2-ONE (A) + 1-OXA-13-CYCLOHEXADECEN-2-ONE
[8]7-ISOPROPYL-2H,4H-1,5-BENZODIOXEPIN-3-ONE
[9](+−)-(3E)-3-methyl-4-(2,6,6-trimethyl-2-cyclohexen-1-yl)-3-buten-2-one (A) + (+−)-(1E)-1-(2,6,6-trimethyl-2-cyclohexen-1-yl)-1-penten-3-one (B)
[10]1-(3,3-dimethyl-1-cyclohexen-1-yl)-4-penten-1-one (A) + 1-(5,5-dimethyl-1-cyclohexen-1-yl)-4-penten-1-one (B)
[11]PENTYL 2-HYDROXYBENZOATE
DECO: discoloration
CL: cloud
VCL: very cloud
WH: white
VCOBR: very brown color
COPI: ping color Example 2

Sensory Evaluation of a Spray Deodorant Formulation According to Some Aspects Presented Herein Test formulations comprising either fragrance formulation 1 containing the β-thio carbonyl derivative profragrance of formula (I), commercially available as HALOSCENT®-D, at the amounts indicated, or fragrance formulation 1 containing the 0-thio carbonyl derivative profragrance of formula (I), commercially available as HALOSCENT®-I were formulated as deodorant sprays.

One gram of each of the test formulation was applied to separate 2-3 year old cotton t-shirts. In parallel, control formulations, comprising fragrance formulation alone (i.e., lacking the β-thio carbonyl derivative profragrance of formula (I)) were similarly applied to separate t-shirts.

A minimum of 18 skilled panelists were asked to evaluate the intensity of the fragrance of the slides, in a blind, balanced, randomized study, with a 20 second break between samples.

The panelists were asked to rank the intensity of the fragrance from 0 (not perceptible), to 10 (very strong odour). The results of the evaluation were analyzed using Analysis of Variance with Duncan's post-hoc analysis ($\alpha$=0.05). The analyzed results are shown in FIG. 1, where the average for each sample at the times indicated are shown. The error bars indicate the 95% confidence level. *=a significant difference at 99.9%; =a significant difference at 99%; *=significant difference at 95%; NS=no significant difference.

Referring to FIG. 1, significant increases in the perceived intensities of fragrance formulation 1 containing either 3% of the β-thio carbonyl derivative profragrance of formula (I), commercially available as HALOSCENT®-I, or 1.2% of the β-thio carbonyl derivative profragrance of formula (I), commercially available as HALOSCENT®-D were observed immediately after application.

TABLE 9

Fragrance Formulation 1 Constituents, as Determined by GC

| Weight % (determined via GC) | Chemical Name |
|---|---|
| 0.25% | Pentanoic acid, 2-methyl-, ethyl ester |
| 0.25% | Oils, pine |
| 0.65% | Hexanoic acid, ethyl ester |
| 0.15% | 3-Hexen-1-ol, acetate, (Z)- |
| 20.35% | Propanol, oxybis- |
| 0.70% | Cyclohexene, 1-methyl-4-(1-methylethenyl)-, (R)- |
| 0.20% | 1,4-Cyclohexadiene, 1-methyl-4-(1-methylethyl)- |
| 2.70% | 7-Octen-2-ol, 2,6-dimethyl- |
| 1.75% | 3-Octanol, 3,7-dimethyl- |
| 1.50% | Acetic acid, phenylmethyl ester |
| 1.30% | Heptanoic acid, 2-propenyl ester |

TABLE 9-continued

Fragrance Formulation 1 Constituents, as Determined by GC

| Weight % (determined via GC) | Chemical Name |
|---|---|
| 1.35% | Benzenemethanol, .alpha.-methyl-, acetate |
| 5.00% | 2h-Pyran-4-ol, tetrahydro-4-methyl-2-(2-methylpropyl)- |
| 1.00% | Acetyl diisoamylene |
| 3.80% | Cyclohexanol, 2-(1,1-dimethylethyl)-, acetate |
| 7.00% | Cyclohexanol, 4-(1,1-dimethylethyl)-, acetate |
| 0.05% | Benzoic acid, 2-(methylamino)-, methyl ester |
| 0.50% | 2H-1-Benzopyran-2-one |
| 0.05% | Bicyclo[7.2.0]undec-4-ene, 4,11,11-trimethyl-8-methylene-, [1R-(1R*,4E,9S*)]- |
| 0.50% | 2(3H)-Furanone, dihydro-5-octyl- |
| 0.40% | (2,5-Dimethyl-2,3 -dihydro-1H-inden-2-yl)methanol |
| 0.70% | Butanoic acid, 1,1-dimethyl-2-phenylethyl ester |
| 2.00% | Phenol, 2,6-bis(1,1-dimethylethyl)-4-methyl- |
| 0.30% | 2-Butanone, 4-(4-hydroxyphenyl)- |
| 1.80% | 2(3H)-Furanone, 5-heptyldihydro- |
| 1.05% | 2-Buten-1-ol, 2-ethyl-4-(2,2,3-trimethyl-3-cyclopenten-1-yl)- |
| 15.00% | Cyclopentaneacetic acid, 3-oxo-2-pentyl-, methyl ester |
| 11.50% | Ethanone, 1-(1,2,3,4,5,6,7,8-octahydro-2,3,8,8-tetramethyl-2-naphthalenyl)- |
| 5.00% | Benzoic acid, 2-hydroxy-, hexyl ester |
| 0.20% | Naphtho[2,1-b]furan, dodecahydro-3a,6,6,9a-tetramethyl- |
| 0.40% | Ethanone, 1-(2,3,4,7,8,8a-hexahydro-3,6,8,8-tetramethyl-1H-3a,7-methanoazulen-5-yl)-, [3R-(3.alpha.,3a.beta.,7.beta.,8a.alpha.)]- |
| 0.70% | Oxacyclohexadec-12-en-2-one, (12E)- |
| 11.00% | 1,4-Dioxacycloheptadecane-5,17-dione |
| 0.90% | Propanoic acid, 3,3'-thiobis-, didodecyl ester |

Example 3

Sensory Evaluation of a Spray Deodorant Formulation According to Some Aspects Presented Herein A test formulation comprising fragrance formulation 1 containing 1.5% of the β-thio carbonyl derivative profragrance of formula (I), commercially available as HALOSCENT®-D was generated. One gram of each of the test formulation was applied to separate 2-3 year old cotton t-shirts. In parallel, control formulations, comprising fragrance formulation 1 alone were similarly applied to separate t-shirts.

A minimum of 18 skilled panelists were asked to evaluate the intensity of the fragrance of the formulation and the intensity of the perceived malodour, in a blind, balanced, randomized study, with a 20 second break between samples.

15 minutes prior to the study, 0.20 grams of sweat body odour solution was applied to the t-shirts. The panelists were asked to (i) rank the intensity of the fragrance from 0 (not perceptible), to 10 (very strong odour), and (ii) rank the intensity of the perceived malodour from 0 (not perceptible), to 10 (very strong odour). The results of the evaluation were analyzed using Analysis of Variance with Duncan's post-hoc analysis ($\alpha=0.05$), wherein:

$$\% \ MO \ \text{reduction} = \frac{(MO_{negativecontrol} - MO_{testsample}) \times 100}{MO_{negativecontrol} - MO_{positivecontrol}}$$

The results are shown in Table 10 below.

TABLE 10

Percentage Reduction in the Perceived Malodour Intensity

| | Fresh | 6 hours | 24 hours | 48 hours |
|---|---|---|---|---|
| Fragrance formulation 1 containing 1.5% HALOSCENT®-D | 72% | 65% | 40% | 61% |
| Fragrance formulation 1 | 82% | 49% | 59% | 31% |

Referring to Table 10, the test formulation comprising fragrance formulation 1 containing 1.5% HALOSCENTO-D demonstrated a greater percentage reduction in the perceived malodour intensity 48 hours after application than the control formulation. However, at the other times tested, the test formulation performed either as well as, or slightly less well than the control formulation.

Example 4

Sensory Evaluation of a Spray Deodorant Formulation According to Some Aspects Presented Herein—Performance on Skin Test formulations were generated according to Table 11 below, containing a β-thio carbonyl derivative profragrance of formula (I). Parallel control formulations were also generated.

TABLE 11

Formulations Tested

| Formulation[12] | Results shown in FIG. |
|---|---|
| 1.5% of a formulation comprising fragrance formulation 2 containing 1.2% of the β-thio carbonyl derivative profragrance of formula (I), commercially available as HALOSCENT®-D | 2 |
| 2.4% of a formulation comprising fragrance formulation 3 containing 2.4% of the β-thio carbonyl derivative profragrance of formula (I), commercially available as HALOSCENT®-D | 3 |
| 2.3% of a formulation comprising fragrance formulation 4[13] containing 2.3% of the β-thio carbonyl derivative profragrance of formula (I), commercially available as HALOSCENT®-D | 4 |
| 1.5% of a formulation comprising fragrance formulation 5 containing 1.2% of the β-thio carbonyl derivative profragrance of formula (I), commercially available as HALOSCENT®-D | 5 |
| 1.5% of a formulation comprising fragrance formulation 1 containing 1.2% of the β-thio carbonyl derivative profragrance of formula (I), commercially available as HALOSCENT®-D 12 | 6 |
| 1.5% of a formulation comprising fragrance formulation 1 containing 1.2% of the β-thio carbonyl derivative profragrance of formula (I), commercially available as HALOSCENT®-I | 7 |
| 1.5% of a formulation comprising fragrance formulation 6 containing 2.6% of the β-thio carbonyl derivative profragrance of formula (I), commercially available as HALOSCENT®-D | 8 |

[12] See Tables 12-15 for constituents, as determined by GC.
[13] As used in the deodorant product sold by Nivea, known as "Freshpetal & Care".

Panelists (20 minimum) were asked to wash both armpits with the supplied unperfumed shower gel, and spray the deodorant formulations directly onto their armpit for 2 seconds from approximately 15 cm away from the armpit (test on one, control on the other). The panelists were asked to evaluate the fragrance intensity, through a t-shirt, at the times indicated in the Figures. Additionally, the panelists were asked to evaluate freshness, and sweat masking.

The results of the evaluation were analyzed using Analysis of Variance with Duncan's post-hoc analysis ($\alpha=0.05$). The error bars indicate the 95% confidence level. *=a significant difference at 99.9%; =a significant difference at 99%; *=significant difference at 95%; NS=no significant difference.

Referring to FIGS. 2 through 9, deodorant formulations containing the β-thio carbonyl derivative profragrance of formula (I) performed either the same, or better than control deodorant formulations. However, some panelists reported the test formulations were fresher, and masked sweat malodour better (see, for example, FIG. 9).

TABLE 12

Fragrance Formulation 2 Constituents, as Determined by GC

| Weight % (determined via GC) | Chemical Name |
|---|---|
| 2.1% | Acetic acid, phenylmethyl ester |
| 1.2% | Benzeneethanol, .alpha.,.alpha.-dimethyl-, acetate |
| 0.4% | Acetic acid, hexyl ester |
| 0.1% | 3-Hexen-1-ol, acetate, (Z)- |
| 0.1% | 2-Buten-1-ol, 3-methyl-, acetate |
| 0.7% | Oxacycloheptadec-10-en-2-one |
| 2.5% | 2(3H)-Furanone, 5-heptyldihydro- |
| 0.3% | Naphtho[2,1-b]furan, dodecahydro-3a,6,6,9a-tetramethyl- |
| 1.2% | 6-Octen-1-ol, 3,7-dimethyl- |
| 0.5% | Cyclohexanepropanoic acid, 2-propenyl ester |
| 2.1% | 7-Octen-2-ol, 2,6-dimethyl- |
| 1.8% | 1,6-Nonadien-3-ol, 3,7-dimethyl- |
| 1.4% | Benzenepropanal, 4-ethyl-.alpha.,.alpha.-dimethyl- |
| 8.2% | Oxacyclohexadec-12-en-2-one, (12E)- |
| 10.0% | 1,6-Octadien-3-ol, 3,7-dimethyl- |
| 2.4% | Cyclohexanemethanol, 4-(1-methylethyl)-, cis- |
| 1.3% | 5-Cyclopentadecen-1-one, 3-methyl- |
| 37.8% | Cyclopentaneacetic acid, 3-oxo-2-pentyl-, methyl ester |
| 0.2% | Butanoic acid, 2-methyl-, ethyl ester |
| 6.5% | 2h-Pyran-4-ol, tetrahydro-4-methyl-2-(2-methylpropyl)- |
| 0.4% | Benzenepentanol, .gamma.-methyl- |
| 0.4% | Propanoic acid, phenylmethyl ester |
| 5.9% | 3-Cyclopentene-1-butanol, .alpha.,.beta.,2,2,3-pentamethyl- |
| 10.0% | 3-Octanol, 3,7-dimethyl- |
| 0.2% | 3-Decen-5-ol, 4-methyl- |
| 0.1% | Ionone |
| 0.2% | 3-Cyclohexene-1-carboxaldehyde, 2,4-dimethyl- |
| 1.8% | Cyclohexene, 1-methyl-4-(1-methylethenyl)-, (R)- |

TABLE 13

Fragrance Formulation 3 Constituents, as Determined by GC

| Weight % (determined via GC) | Chemical Name |
|---|---|
| 6.00 | Acetic acid, phenylmethyl ester |
| 1.50 | Benzeneethanol, .alpha.,.alpha.-dimethyl-, acetate |
| 0.20 | 6-Octen-1-ol, 3,7-dimethyl-, acetate |
| 2.60 | 1,6-Octadien-3-ol, 3,7-dimethyl-, 3-acetate |
| 0.10 | 3-Hexen-1-ol, acetate, (Z)- |
| 0.20 | Benzenemethanol, .alpha.-methyl-, acetate |
| 1.00 | Acetic acid, hexyl ester |
| 0.30 | Benzenepropanol |
| 1.00 | Benzaldehyde, 4-methoxy- |
| 0.30 | Benzoic acid, 2-amino-, methyl ester |
| 0.30 | 2H-1,5-Benzodioxepin-3(4H)-one, 7-methyl- |
| 0.30 | Bicyclo[2.2.1]heptan-2-one, 1,7,7-trimethyl- |
| 0.30 | Naphtho[2,1-b]furan, dodecahydro-3a,6,6,9a-tetramethyl- |
| 0.50 | 2-Cyclopenten-1-one, 3-methyl-2-(2-pentenyl)-, (Z)- |
| 2.00 | 6-Octen-1-ol, 3,7-dimethyl- |
| 0.80 | 2-Pentylcyclopentan-1-ol |
| 0.40 | Benzenepropanal, .alpha.-methyl-4-(1-methylethyl)- |
| 1.00 | 2,4-Cyclohexadiene-1-carboxylic acid, 2,6,6-trimethyl-, ethyl ester |
| 2.00 | 2-Buten-1-ol, 2-ethyl-4-(2,2,3-trimethyl-3-cyclopenten-1-yl)- |
| 0.40 | 2(3H)-Furanone, 5-hexyldihydro- |
| 0.30 | 1-Octanol, 3,7-dimethyl- |
| 5.00 | Propanol, oxybis- |
| 0.10 | 2H-Pyran, tetrahydro-4-methyl-2-phenyl-, (2R,4S)-rel- |
| 2.20 | Oxacyclohexadecan-2-one |
| 6.00 | 2h-Pyran-4-ol, tetrahydro-4-methyl-2-(2-methylpropyl)- |
| 0.40 | 2,6-Octadien-1-ol, 3,7-dimethyl-, (E)- |
| 4.50 | Oxacyclohexadec-12-en-2-one, (12E)- |
| 0.90 | 1,3-Benzodioxole-5-carboxaldehyde |
| 0.20 | Indeno[1,2-d]-1,3-dioxin, 4,4a,5,9b-tetrahydro- |
| 15.00 | Ethanone, 1-(1,2,3,4,5,6,7,8-octahydro-2,3,8,8-tetramethyl-2-naphthalenyl)- |
| 0.50 | (2,5-Dimethyl-2,3-dihydro-1H-inden-2-yl)methanol |
| 5.60 | Cyclohexene, 1-methyl-4-(1-methylethenyl)-, (R)- |
| 6.40 | 1,6-Octadien-3-ol, 3,7-dimethyl- |
| 0.80 | Cyclohexanemethanol, 4-(1-methylethyl)-, cis- |
| 1.80 | 4-Penten-1-one, 1-(5,5-dimethyl-1-cyclohexen-1-yl)- |
| 0.15 | 2H-Pyran, tetrahydro-4-methyl-2-(2-methyl-1-propenyl)- |
| 2.75 | Benzeneethanol |
| 11.00 | Benzenepentanol, .gamma.-methyl- |
| 8.70 | Benzoic acid, 2-hydroxy-, hexyl ester |
| 5.50 | Ionone |

TABLE 14

Fragrance Formulation 5 Constituents, as Determined by GC

| Weight % (determined via GC) | Chemical Name |
|---|---|
| 0.20 | 2,6-Octadien-1-ol, 3,7-dimethyl-, acetate, (E)- |
| 0.60 | 1,6-Octadien-3-ol, 3,7-dimethyl-, 3-acetate |
| 0.20 | 2,6-Octadien-1-ol, 3,7-dimethyl-, acetate, (Z)- |
| 3.50 | 3-Cyclohexene-1-methanol, .alpha.,.alpha.,4-trimethyl-, acetate |
| 0.05 | Decanal |
| 0.05 | Undecanal |
| 0.45 | Bicyclo[2.2.1]heptan-2-ol, 1,7,7-trimethyl-, (1S,2R,4S)- |

TABLE 14-continued

Fragrance Formulation 5 Constituents, as Determined by GC

| Weight % (determined via GC) | Chemical Name |
|---|---|
| 0.10 | 2H-1,5-Benzodioxepin-3(4H)-one, 7-methyl- |
| 1.45 | Naphtho[2,1-b]furan, dodecahydro-3a,6,6,9a-tetramethyl- |
| 0.60 | 6-Octenenitrile, 3,7-dimethyl- |
| 1.40 | Cyclohexanepropanol, .alpha.,.alpha.-dimethyl- |
| 1.20 | 2H-1-Benzopyran-2-one |
| 18.00 | 7-Octen-2-ol, 2,6-dimethyl- |
| 0.10 | 2-Oxabicyclo[2.2.2]octane, 1,3,3-trimethyl- |
| 2.80 | Oxacyclohexadecan-2-one |
| 4.50 | 2h-Pyran-4-ol, tetrahydro-4-methyl-2-(2-methylpropyl)- |
| 4.50 | Oxacyclohexadec-12-en-2-one, (12E)- |
| 15.00 | Cyclopentaneacetic acid, 3-oxo-2-pentyl-, methyl ester |
| 23.00 | Ethanone, 1-(1,2,3,4,5,6,7,8-octahydro-2,3,8,8-tetramethyl-2-naphthalenyl)- |
| 0.60 | 1,6-Octadien-3-ol, 3,7-dimethyl- |
| 18.30 | Tetradecanoic acid, 1-methylethyl ester |
| 0.60 | Cyclohexanepropanol, 2,2,6-trimethyl-.alpha.-propyl- |
| 0.10 | 3-Cyclohexen-1-ol, 4-methyl-1-(1-methylethyl)- |
| 0.30 | Terpineol |
| 0.30 | Cyclopentanone, 2,2,5-trimethyl-5-pentyl- |
| 2.10 | Ethanone, 1-(2,3,4,7,8,8a-hexahydro-3,6,8,8-tetramethyl-1H-3a,7-methanoazulen-5-yl)-, [3R-(3.alpha.,3a.beta.,7.beta.,8a. alpha.)]- |

TABLE 15

Fragrance Formulation 6 Constituents, as Determined by GC

| Weight % (determined via GC) | Chemical Name |
|---|---|
| 0.4% | Oils, pine |
| 0.1% | 3-Hexen-1-ol, acetate, (Z)- |
| 0.1% | Benzene, 1-methyl-4-(1-methylethyl)- |
| 3.6% | Cyclohexene, 1-methyl-4-(1-methylethenyl)-, (R)- |
| 0.4% | 1,4-Cyclohexadiene, 1-methyl-4-(1-methylethyl)- |
| 27.0% | 7-Octen-2-ol, 2,6-dimethyl- |
| 0.1% | Cyclohexene, 1-methyl-4-(1-methylethylidene)- |
| 0.1% | Heptanoic acid, 2-propenyl ester |
| 0.4% | 2,6-Octadienal, 3,7-dimethyl- |
| 0.3% | Cyclohexanol, 2-(1,1-dimethylethyl)-, acetate |
| 0.1% | Benzeneethanol, .alpha.,.alpha.-dimethyl-, acetate |
| 0.1% | 2,6-Octadien-1-ol, 3,7-dimethyl-, acetate, (E)- |
| 0.1% | Propanoic acid, 2-methyl-, 2-phenylethyl ester |
| 0.8% | Benzenepropanoic acid, 3,5-bis(1,1-dimethylethyl)-4-hydroxy-, 2,2-bis[[3-[3,5-bis(1,1-dimethylethyl)-4-hydroxyphenyl]-1-oxopropoxy]methyl]- -1,3-propanediyl ester |
| 1.5% | Propanoic acid, 3,3'-thiobis-, didodecyl ester |
| 0.1% | 2(3H)-Furanone, 5-heptyldihydro- |
| 0.5% | 1,4-Cyclohexanedicarboxylic acid, diethyl ester |
| 2.5% | Cyclohexanepropanol, 2,2,6-trimethyl-.alpha.-propyl- |
| 11.1% | 1H-3a,7-Methanoazulene, octahydro-6-methoxy-3,6,8,8-tetramethyl-, [3R-(3.alpha.,3a.beta.,6.beta.,7.beta.,8a.alpha.)]- |
| 11.0% | Cyclopentaneacetic acid, 3-oxo-2-pentyl-, methyl ester |
| 25.0% | Ethanone, 1-(1,2,3,4,5,6,7,8-octahydro-2,3,8,8-tetramethyl-2-naphthalenyl)- |

TABLE 15-continued

Fragrance Formulation 6 Constituents, as Determined by GC

| Weight % (determined via GC) | Chemical Name |
|---|---|
| 4.5% | Cyclododecane, (ethoxymethoxy)- |
| 2.5% | Naphtho[2,1-b]furan, dodecahydro-3a,6,6,9a-tetramethyl- |
| 8.0% | 1,4-Dioxacycloheptadecane-5,17-dione |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. An antiperspirant or deodorant composition, comprising:
   a. a carrier;
   b. a perfuming composition, comprising:
      i. at least one β-thio carbonyl derivative profragrance of formula (I)

$$P\sim\!\!\sim\!\!S\text{—}R \qquad (I)$$

wherein the wavy line indicates the location of the bond between said P and the sulfur atom, P represents a group of the formulae (P-1) to (P-9), in the form of any one of their isomers:

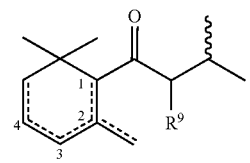

(P-1)

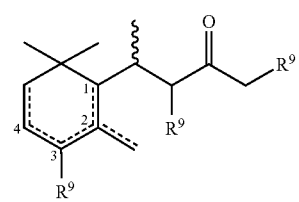

(P-2)

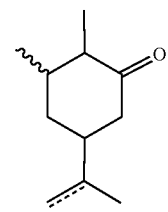

(P-3)

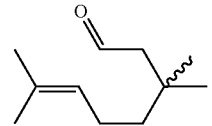

(P-4)

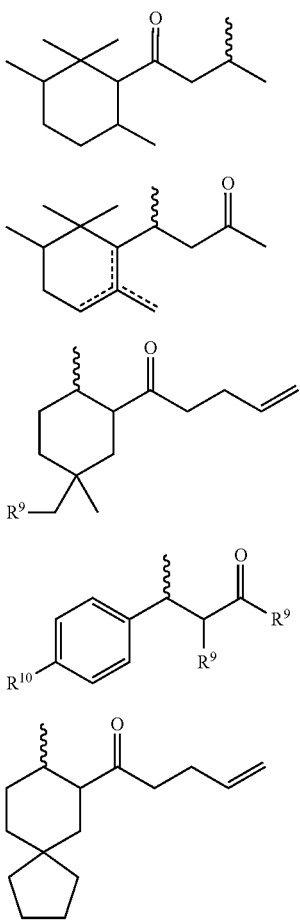

in which formulae, the wavy lines have the meaning indicated above and the dotted lines represent a single or double bond; $R^9$ represents a hydrogen atom or a methyl group; $R^{10}$ represents a hydrogen atom, a hydroxy or methoxy group, or a $C_1$-$C_4$ linear or branched alkyl group; and R represents a linear or branched alkyl group having from 8 to 15 carbon atoms, optionally comprising a carboxylic functional group which is not directly linked to the sulfur atom; and ii. a free perfume; and c. an antiperspirant active ingredient or a deodorant active ingredient;

wherein the at least one β-thio carbonyl derivative profragrance of formula (I) is present in an amount from 0.001 to 10 wt %, relative to the total weight of the composition;

wherein the at least one β-thio carbonyl profragrance derivative of formula (I) comprises 3-(dodecylthio)-1-(2,6,6-trimethylcyclohex-3-en-1-yl)butan-1-one; and wherein the free perfume is present in an amount from 0.0001 to 6 wt %, relative to the total weight of the composition.

2. The composition of claim 1, further comprising an encapsulated perfume.

3. The composition of claim 1, comprising an antiperspirant active ingredient.

4. The composition of claim 1, wherein the at least one β-thio carbonyl derivative profragrance of formula (I) is present in an amount from 0.001 to 7 wt %, relative to the total weight of the composition.

5. The composition of claim 1, wherein the at least one β-thio carbonyl derivative profragrance of formula (I) is present in an amount from 0.001 to 5 wt %, relative to the total weight of the composition.

6. The composition of claim 1, wherein the free perfume is present in an amount from 0.0001 to 0.4 wt %, relative to the total weight of the composition.

7. The composition of claim 1, wherein the composition is formulated as an antiperspirant or deodorant product selected from the group consisting of: a stick and an aerosol.

8. The composition of claim 1, wherein the composition comprises less than 55 wt % of water, relative to the total weight of the composition.

9. The composition of claim 1, wherein the composition is water-free.

10. The composition of claim 1, wherein the free perfume is selected from the group consisting of: geraniol, citronellol, dihydromyrcenol, hydroxycitronellal, 3-Methy 1-5-cyclopentadecen-1-one, cyclopentadecanone, (1S,1'R)-[1-(3',3'-Dimethyl-1'-cyclohexyl)ethoxycarbonyl]methyl propanoate, pentadecenolide, 7-Methyl-2H,4H-1,5-benzodioxepin-3-one, indole, 3-methyl-4-(2,6,6-trimethyl-2-cyclohexen-1-yl)-3-buten-2-one, 1-(5,5-dimethylcyclohex-1-en-1-yl)pent-4-en-1-one, amyl salicyclate, methyl dihydrojasmonate, cyclohexyl salicylate and mixtures thereof.

11. The composition of claim 1, wherein the free perfume comprises at least one perfuming ingredient selected from the group consisting of 1-(octahydro-2,3,8,8-tetramethyl-2-naphtalenyl)-1-ethanone; dipropylene glycol, 2,4-Dimethyl-3-cyclohexene-1-carbaldehyde, dodecahydro-3a,6,6,9a-tetramethyl-naphtho[2,1-b]furan; linalool, coumarin, (Z)-3-hexen-1-ol, allyl amyl glycolate, 2-tut-butyl-1-cyclohexyl acetate; styrallyl acetate, 3-(4-tert-butylphenyl)-2-methylpropanal, 1,4-dioxa-5,17-cycloheptadecanedione, crystal moss, gamma undecalactone, (Z)-hex-3-en-1-yl acetate, neo (tetrahydro-2-isobutyl-4-methyl-4(2H)-pyranol); damascone alpha, benzyl acetate, ethylvanillin, ethyl 2-methylpentanoate, isopropyl myristate, $C_{10}$ aldehyde, rose oxide, hexylcinnamic aldehyde, hexyl salicylate, (1'R,E)-2-ethyl-4-(2',2',3'-trimethyl-3'-cyclopenten-1'-yl)-2-buten-1-ol and mixtures thereof.

12. A method for treating, masking, eliminating, preventing, or reducing body malodour of a subject in need thereof, the method comprising applying to the subject's skin, an antiperspirant or deodorant composition, comprising:

a. a carrier;

b. a perfuming composition, comprising:

i. at least one β-thio carbonyl derivative profragrance of formula (I)

$$P\mathord{\sim\!\!\sim}S-R \quad (I)$$

wherein the wavy line indicates the location of the bond between said P and the sulfur atom, P represents a group of the formulae (P-1) to (P-9), in the form of any one of their isomers:

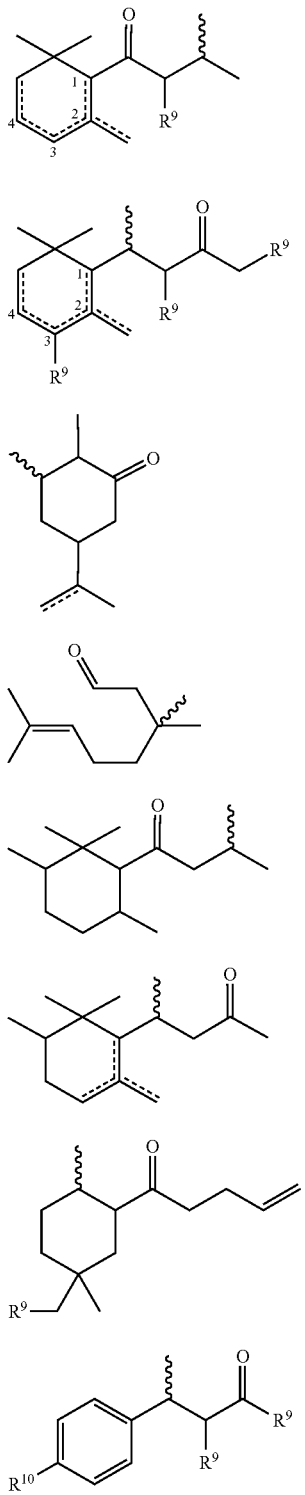

in which formulae, the wavy lines have the meaning indicated above and the dotted lines represent a single or double bond; $R^9$ represents a hydrogen atom or a methyl group; $R^{10}$ represents a hydrogen atom, a hydroxy or methoxy group, or a $C_1$-$C_4$ linear or branched alkyl group; and R represents a linear or branched alkyl group having from 8 to 15 carbon atoms, optionally comprising a carboxylic functional group which is not directly linked to the sulfur atom; and ii. a free perfume; and c. an antiperspirant active ingredient or a deodorant active ingredient;

wherein the at least one β-thio carbonyl derivative profragrance of formula (I) is present in an amount from 0.001 to 10 wt %, relative to the total weight of the composition; and wherein the at least one β-thio carbonyl profragrance derivative of formula (I) comprises 3-(dodecylthio)-1-(2,6,6-trimethylcyclohex-3-en-1-yl)butan-1-one; and wherein the free perfume is present in an amount from 0.0001 to 6 wt %, relative to the total weight of the composition.

13. The composition of claim 1, wherein the carrier is a liquid and is selected from the group consisting of ethanol, water, silicone solvents, and mixtures thereof.

14. The composition of claim 1, wherein the composition is formulated as an antiperspirant or deodorant product selected from the group consisting of wax-based sticks, soap-based sticks, compressed powder sticks, roll-on suspensions or solutions, emulsions, gels, creams, squeeze sprays, pump sprays, and aerosols.

15. The composition of claim 1, wherein the composition comprises less than 70 wt % of water, relative to the total weight of the composition.

16. The method of claim 12, wherein the carrier is a liquid and is selected from the group consisting of ethanol, water, silicone solvents, and mixtures thereof.

17. The method of claim 12, wherein the composition is formulated as an antiperspirant or deodorant product selected from the group consisting of wax-based sticks, soap-based sticks, compressed powder sticks, roll-on suspensions or solutions, emulsions, gels, creams, squeeze sprays, pump sprays, and aerosols.

18. The method of claim 12, wherein the composition comprises less than 70 wt % of water, relative to the total weight of the composition.

* * * * *